US012089882B2

(12) United States Patent
Gregory, II et al.

(10) Patent No.: US 12,089,882 B2
(45) Date of Patent: Sep. 17, 2024

(54) METHOD AND SYSTEM FOR ASSEMBLING A STRUCTURE TO SECURE TO OPPOSITE SIDES OF A FRACTURE IN A BONE OF A SUBJECT

(71) Applicant: FUSION INNOVATIONS, LLC, Sanford, FL (US)

(72) Inventors: Richard O. Gregory, II, Rock Hill, SC (US); David A. Walsh, Reading, MA (US); Mark Schumacher, Sanford, FL (US)

(73) Assignee: FUSION INNOVATIONS, LLC, Sanford, FL (US)

( * ) Notice: Subject to any disclaimer, the term of this patent is extended or adjusted under 35 U.S.C. 154(b) by 1082 days.

(21) Appl. No.: 16/864,001

(22) Filed: Apr. 30, 2020

(65) Prior Publication Data

US 2020/0345399 A1 Nov. 5, 2020

Related U.S. Application Data

(60) Provisional application No. 62/841,018, filed on Apr. 30, 2019.

(51) Int. Cl.
*A61B 17/80* (2006.01)
*A61B 17/82* (2006.01)
(52) U.S. Cl.
CPC ...... *A61B 17/8052* (2013.01); *A61B 17/8076* (2013.01); *A61B 17/82* (2013.01)

(58) Field of Classification Search
CPC . A61B 17/80; A61B 17/8023; A61B 17/8052; A61B 17/8057; A61B 17/8061; A61B 17/8066; A61B 17/8071; A61B 17/8076; A61B 17/808
See application file for complete search history.

(56) References Cited

U.S. PATENT DOCUMENTS

| | | |
|---|---|---|
| 5,549,612 A | 8/1996 | Yapp et al. |
| 5,616,144 A | 4/1997 | Yapp et al. |
| 5,735,853 A | 4/1998 | Olerud |
| 6,051,007 A | 4/2000 | Hogendijk et al. |
| 6,129,728 A | 10/2000 | Schumacher et al. |
| 6,325,803 B1 | 12/2001 | Schumacher et al. |
| 6,336,927 B2 | 1/2002 | Rogozinski |
| 6,520,965 B2 | 2/2003 | Chervitz et al. |
| 6,540,769 B1 | 4/2003 | Miller, III |

(Continued)

*Primary Examiner* — Si Ming Ku
(74) *Attorney, Agent, or Firm* — Timothy H. Van Dyke; Wolter, Van Dyke, Davis, PLLC

(57) ABSTRACT

A modular system is provided for assembling a structure to secure to opposite sides of a fracture in a bone of a subject. The modular system includes a plate with a perimeter including a plurality of openings. The perimeter defines an interior area within the plate. The modular system also includes a link with one or more openings along a linear axis defining the link. The one or more openings of the link include a connector to receive a fastener to be secured in the bone. The plurality of openings of the plate includes a first opening with an inner diameter configured to removably receive an outer diameter of the connector of the link so that the link is rotatably received within the first opening. A method is also provided for assembling the structure using the modular system and securing the assembled structure to opposite sides of the bone fracture.

22 Claims, 38 Drawing Sheets

(56) References Cited

U.S. PATENT DOCUMENTS

| | | |
|---|---|---|
| 6,969,398 B2 | 11/2005 | Stevens et al. |
| 7,090,676 B2 | 8/2006 | Huebner et al. |
| 7,189,237 B2 | 3/2007 | Huebner |
| D564,097 S | 3/2008 | Olerud |
| 7,695,473 B2 | 4/2010 | Ralph et al. |
| 8,257,355 B2 | 9/2012 | Chin et al. |
| 8,287,542 B2 | 10/2012 | Wolter |
| 8,372,123 B2 | 2/2013 | Smisson, III et al. |
| 8,506,605 B2 | 8/2013 | Bickley et al. |
| 8,668,725 B2 | 3/2014 | Smisson, III et al. |
| 8,795,342 B2 | 8/2014 | Reisberg |
| 9,526,543 B2 | 12/2016 | Castaneda et al. |
| 2005/0240191 A1 | 10/2005 | Albertson et al. |
| 2006/0089648 A1 | 4/2006 | Masini |
| 2006/0116681 A1 | 6/2006 | Bert |
| 2006/0271052 A1 | 11/2006 | Stern |
| 2008/0097445 A1 | 4/2008 | Weinstein |
| 2010/0179552 A1* | 7/2010 | Wolter ............... A61B 17/8057 606/71 |
| 2013/0178906 A1* | 7/2013 | Madjarov ............ A61B 17/823 606/286 |
| 2014/0214091 A1* | 7/2014 | Sixto .................. A61B 17/888 606/286 |
| 2015/0038969 A1 | 2/2015 | Garcia et al. |
| 2016/0000481 A1 | 1/2016 | Ehmke et al. |
| 2016/0317161 A1 | 11/2016 | Garcia et al. |

* cited by examiner

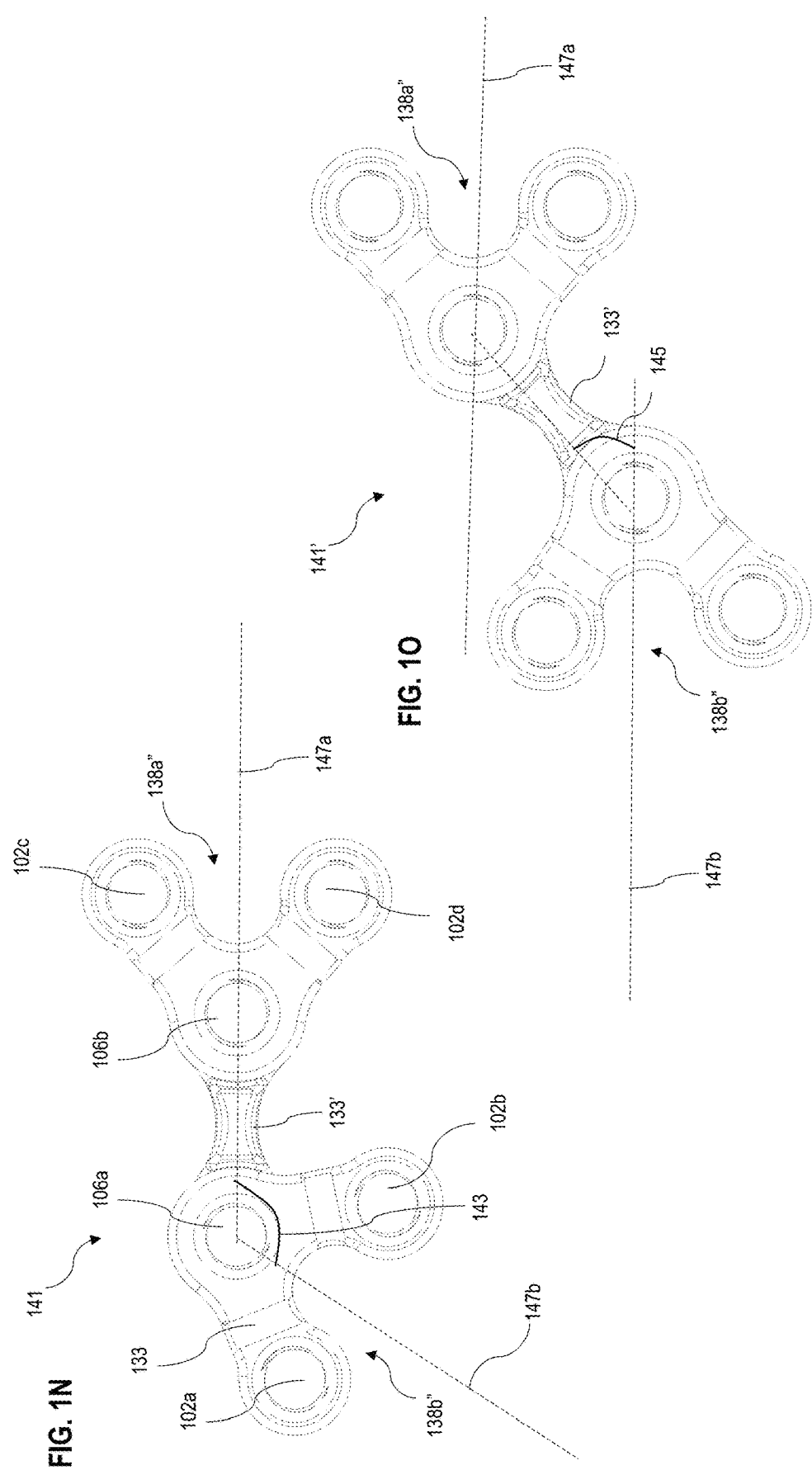

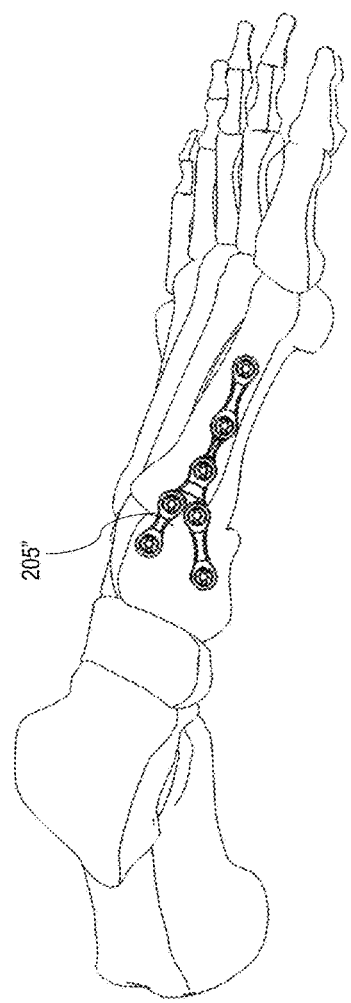
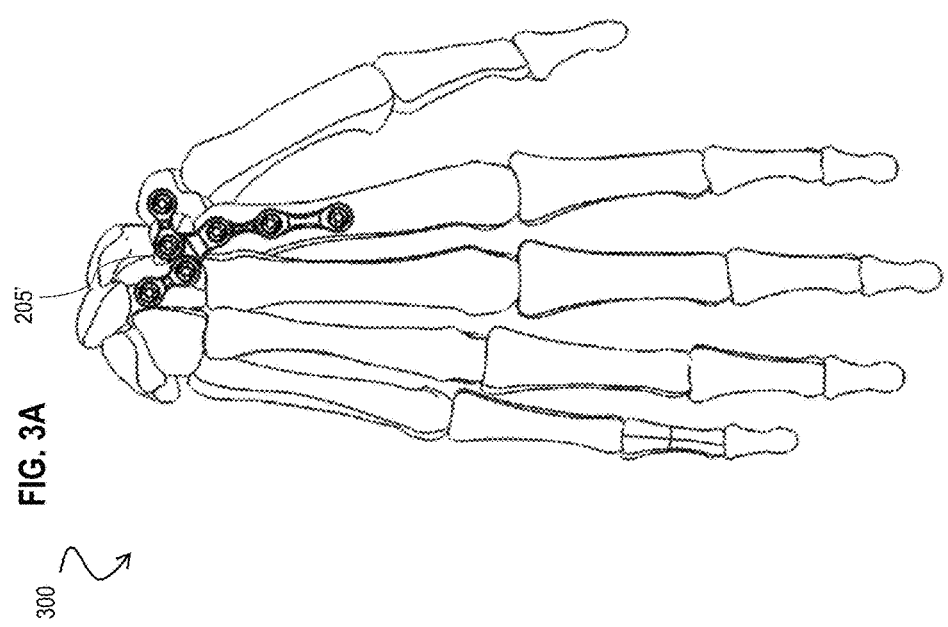

METHOD AND SYSTEM FOR ASSEMBLING A STRUCTURE TO SECURE TO OPPOSITE SIDES OF A FRACTURE IN A BONE OF A SUBJECT

CROSS REFERENCE TO RELATED APPLICATIONS

This application claims benefit of Provisional Application No. 62/841,018, filed Apr. 30, 2019, the entire contents of which is hereby incorporated by reference as if fully set forth herein, under 35 U.S.C. § 119(e).

BACKGROUND

Bone fractures have conventionally been fixed together using a variety of techniques including wire, cable or plates. Wire and cable are conventionally used by wrapping the wire or cable around the bone fracture (e.g. in a direction orthogonal to the bone fracture) and tightened, to fix the opposite sides of the bone fracture together, so that the opposite sides of the bone fracture fuse together over time. For example, U.S. Pat. No. 8,287,542 discloses a system including two or more plates that are interconnected to form a structure that is used to connect to opposite sides of a bone fracture.

SUMMARY

The current inventors have recognized that the system disclosed in the '542 patent is deficient since it only consists of two basic building blocks (e.g. links depicted in FIGS. 8 and 9) that are combined to form the various structures (e.g. depicted in FIGS. 10-14) that are used to connect to opposite sides of a bone fracture. Also, the inventors of the present invention recognized that the building blocks of the '542 patent are limited to links and exclude bone plates. Thus, the inventors of the present invention recognized that the system of the '542 is inherently limited by only including two basic building blocks and further only employing links, consequently limiting the variety of structures that can be formed. The inventors of the present invention recognized that this is disadvantageous to a medical practitioner attempting to build a structure that most closely resembles the bone at opposite sides of the fracture, since different subjects present a variety of bone fractures with distinct characteristics (e.g. dimension, bone quality, etc.). Thus, the inventors of the present invention recognized that it would be advantageous to develop a modular system that could be used to build a structure to connect to opposite sides of a bone structure, where the modular system includes a large number of basic interconnectable building blocks and where the interconnectable building blocks include both plates and links. As a result, the improved modular system can be used to build a structure that can accommodate different subjects that present a variety of bone fractures with different characteristics (e.g. dimension, bone quality, etc.).

In a first set of embodiments, a modular system is provided for assembling a structure to secure to opposite sides of a fracture in a bone of a subject. The modular system includes two or more components including a plate with a perimeter including a plurality of openings, where the perimeter defines an interior area within the plate. The modular system also includes a link with one or more openings along one or more linear axes defining the link. The one or more openings of the link include a connector configured to receive a fastener to be secured in the bone. The plurality of openings of the plate includes a first opening with an inner diameter configured to removably receive an outer diameter of the connector of the link so that the link is rotatably received within the first opening.

In a second set of embodiments, a method is provided for assembling a structure to secure to opposite sides of a fracture in a bone of a subject. The method includes determining one or more characteristics of the bone and assembling a structure using the modular system of claim 1 based on the one or more characteristics of the bone. The method further includes aligning the assembled structure with the fracture in the bone. The method further includes adjusting the structure using the modular system based on the one or more characteristics of the bone and the aligning step, if the assembled structure is not aligned with the fracture. The method further includes securing the assembled structure to opposite sides of the fracture in the bone if the assembled structure is aligned with the fracture.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIGS. 1N through 1P are images that illustrate an example of a first link coupled to a pair of second links for use in the modular system of FIGS. 1A and 1B, according to an embodiment;

FIG. 3A is an image that illustrates a front view of a structure assembled with the modular system of FIGS. 1A-1B and aligned with a fracture in a hand bone of a subject, according to an embodiment;

FIG. 3B is an image that illustrates a front view of a structure assembled with the modular system of FIGS. 1A-1B and aligned with a fracture in a foot bone of a subject, according to an embodiment;

FIGS. 5F through 5L are images that illustrate an example of the tool of FIGS. 5B through 5E being used to perform one or more steps of the method of FIG. 4, according to an embodiment;

DETAILED DESCRIPTION

Figure 1A:
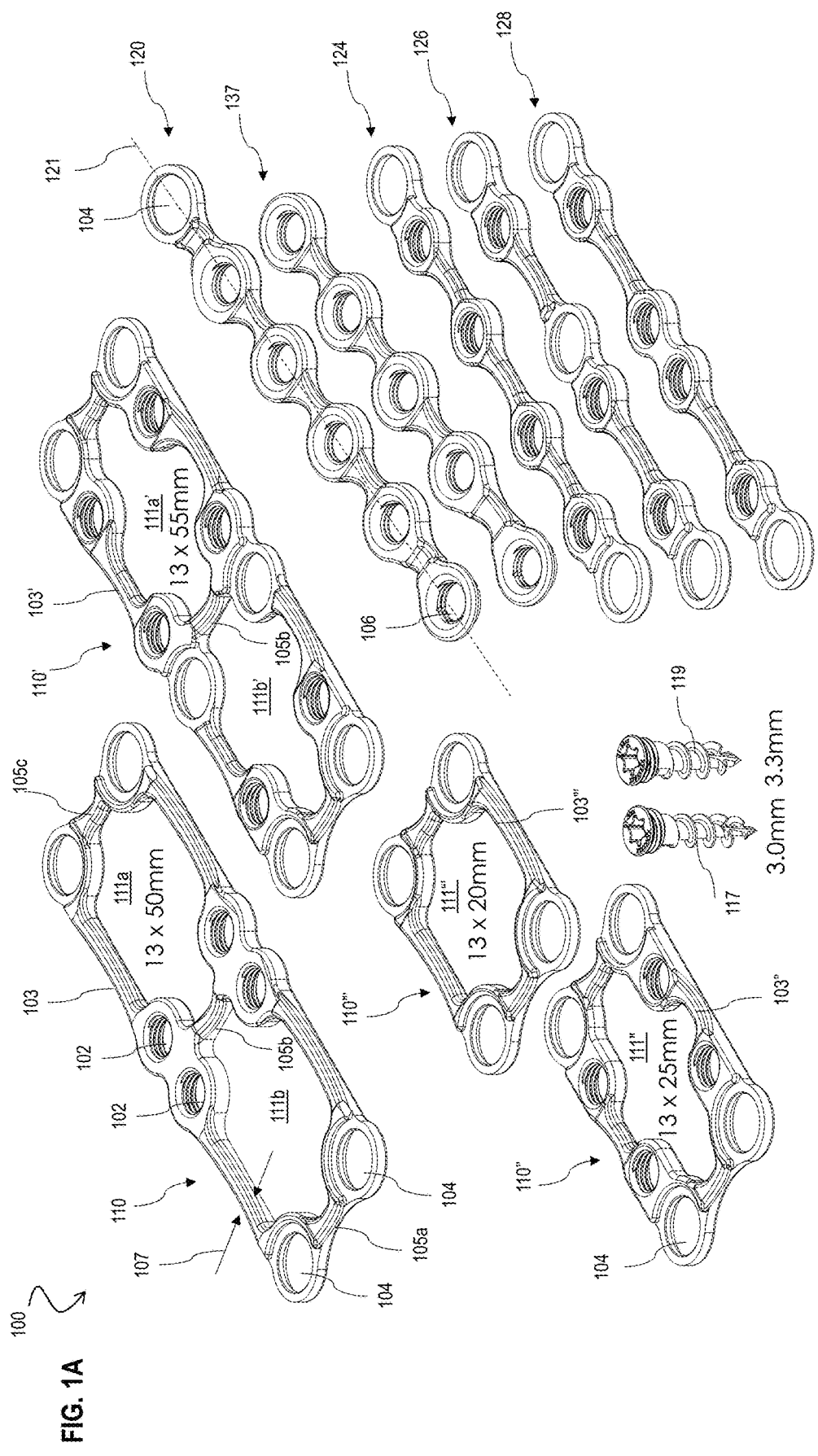
FIG. 1A is an image that illustrates an example of a top perspective view of a modular system including plates and links, according to an embodiment.

A method and apparatus and system are described for assembling a structure to secure to opposite sides of a fracture in a bone of a subject for purposes of fusing the bone along the fracture. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about x" implies a value in the range from 0.5x to 2x, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

For purposes of this description, "fracture" means any break in any bone of a subject, human or non-human, whether an intentional fracture due to surgical intervention to access an area of the subject (e.g. sternum fracture due to sternotomy for open heart surgery) or an accident fracture due to physical trauma. For purposes of this description, "plate" means a component with a perimeter that includes one or more openings in the perimeter and where the perimeter defines an interior open area within the plate. For purposes of this description, "link" means a component with one or more openings that define one or more linear axes of the link. Additionally, a "wye link" does not have openings that define a single linear axis but also do not have the interior "open area" that is included in the plate description above.

Some embodiments of the invention are described below in the context of securing opposite sides of a fracture in a bone together in a subject. In some embodiments, the invention is described in the context of securing opposite sides of a fracture in a bone that was caused due to surgical intervention (e.g. sternotomy due to open heart surgery). In other embodiments, the invention is described in the context of securing opposite sides of a fracture in a bone that was caused due to trauma (e.g. fracture in a bone of the hand or leg or jaw). In other embodiments, the invention is described in the context of removal of bone due to cancer where the structure is used to replace the bone being removed.

Figure 1B:
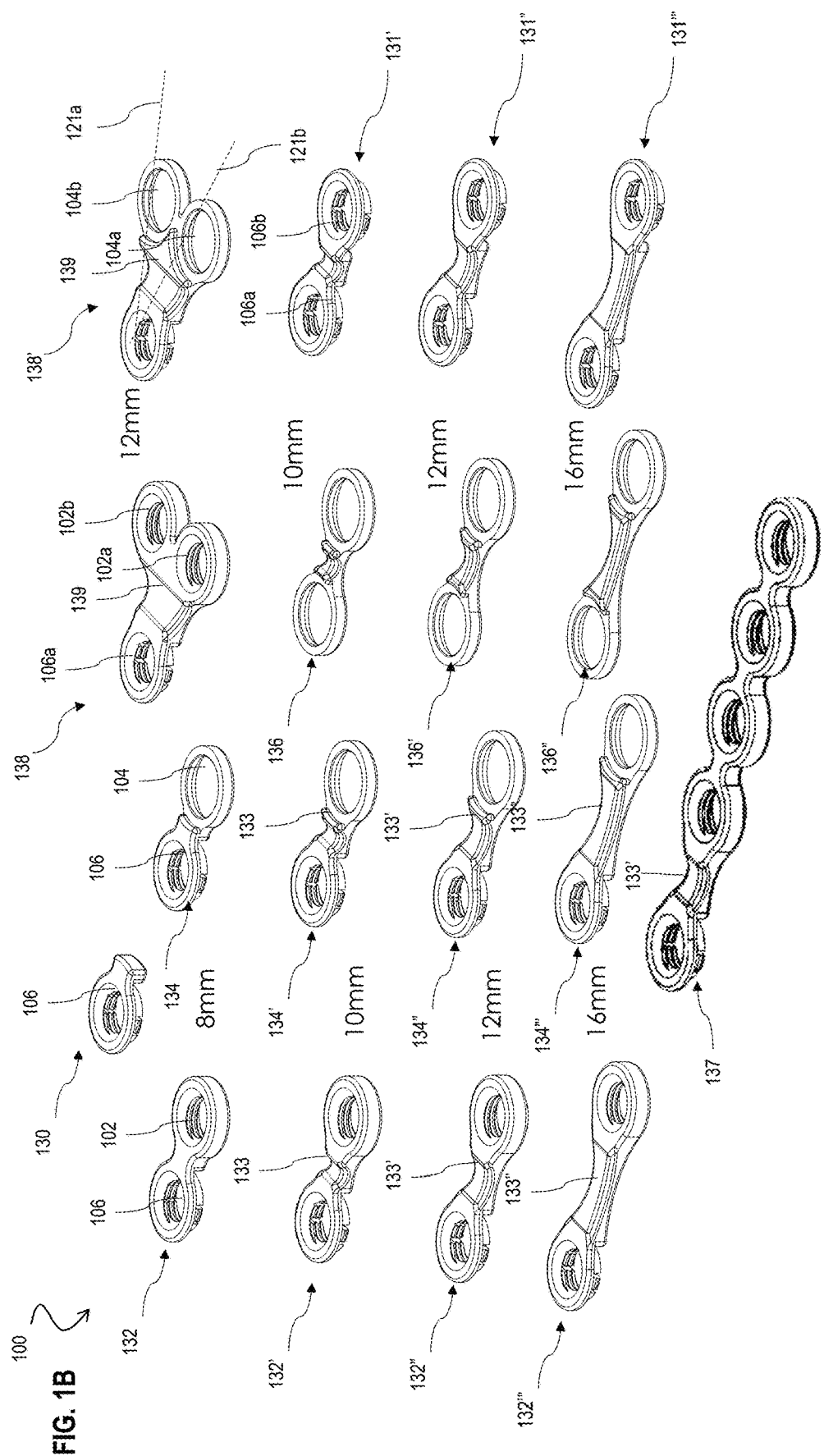
FIG. 1B is an image that illustrates an example of a top perspective view of a modular system including links, according to an embodiment.
Figure 1C:
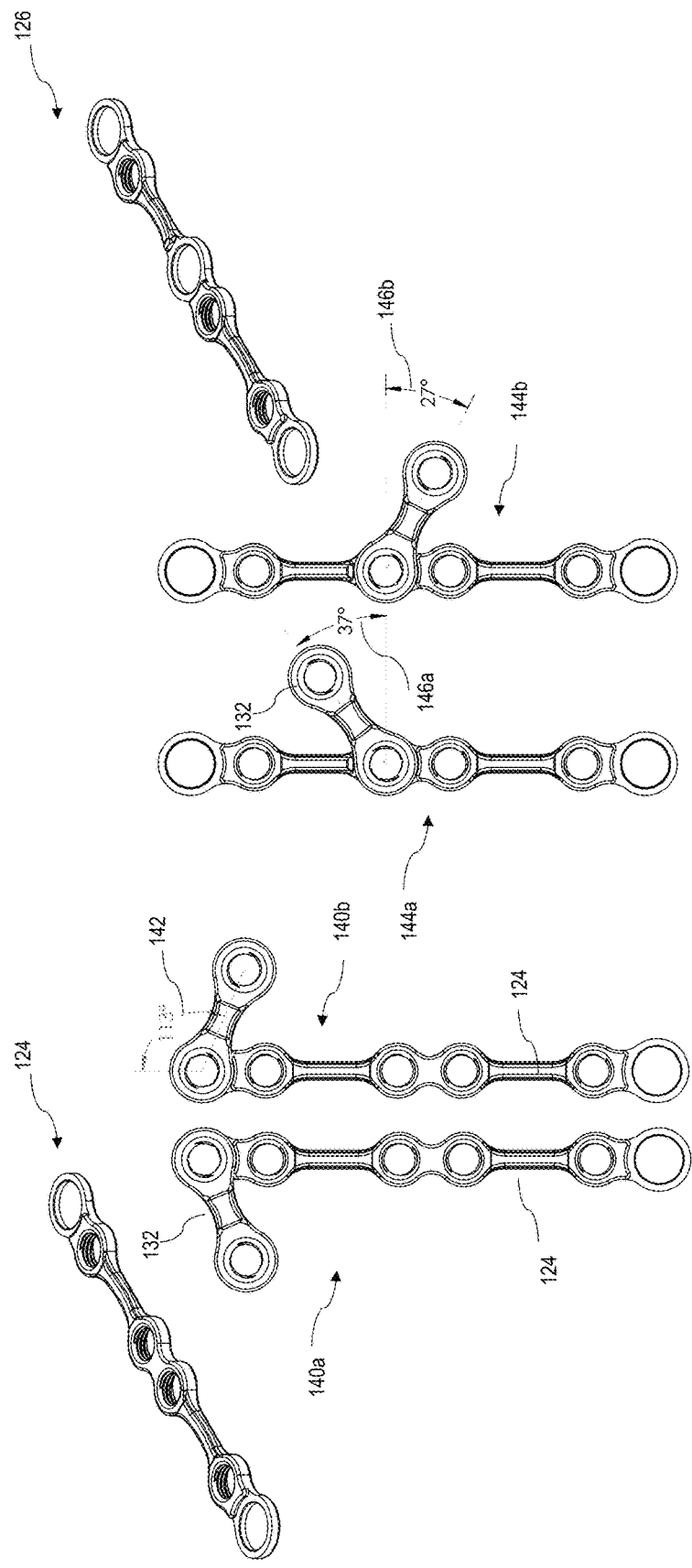
FIG. 1C is an image that illustrates an example of a front view of a first link rotatably coupled to a second link of the modular system of FIGS. 1A-1B, according to an embodiment.
Figure 1E:
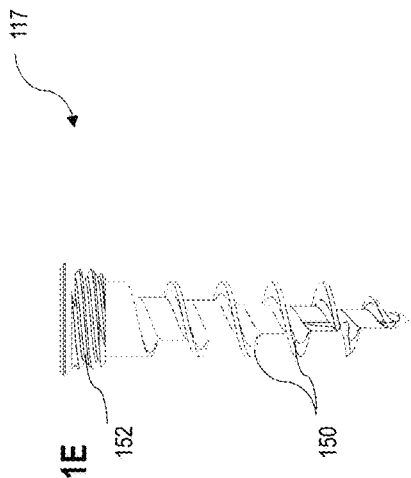
FIG. 1E is an image that illustrates an example of a side view of a fastener of the system of FIG. 1A, according to an embodiment.
Figure 1D:
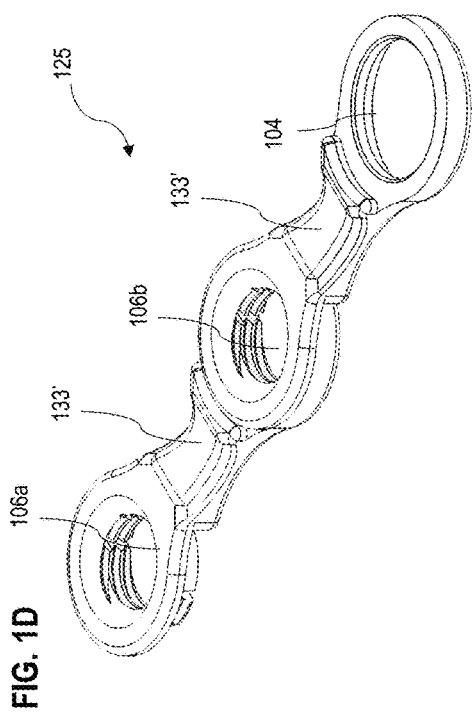
FIG. 1D is an image that illustrates an example of a top perspective view of two interconnected links of the system of FIG. 1A, according to an embodiment.

FIGS. 1A-1B are images that illustrate an example of a top perspective view of a modular system 100 including plates and links, according to an embodiment. Although multiple plates and multiple links are depicted, the modular system 100 need only include one plate or one link and/or at least two components among the plates or links. Additionally, the modular system 100 does not require one or more links or plates that are configured to be connected together and includes one or more fixed components (e.g. plates 110"", 110""' of FIGS. 1L and 1M) that are not connected with another link or plate. In an embodiment, the plates and/or links are made from stainless steel, titanium, titanium alloy, cobalt chrome, a polymer, e.g. Polyether Ether Ketone (PEEK) and/or any material determined to be suitable by one of ordinary skill in the art. However, the plates and/or links need not be made out of any particular material. In an embodiment, the modular system 100 includes a plate (110, 110', 110", 110"') with a perimeter (103, 103', 103", 103"') that includes a plurality of openings including a terminal 102 and a ring connector 104 adjacent one of the openings. In still other embodiments, the modular system 100 includes a plate (110"", 110""') as shown in FIGS. 1L and 1M that include multiple terminals 102 and exclude ring connectors 104. In one embodiment, the terminals 102 are adjacent one of the openings and are configured to receive (e.g. are internally threaded) a fastener 117, 119 (e.g. externally threaded screw) that is fastened into the bone below the plate. In an example embodiment, an inner diameter the terminals 102 is about 3.5 mm or in a range from about 3.5 mm to about 4.7 mm and/or in a range from about 2 mm to about 6 mm. In another embodiment, the ring connectors 104 are non-threaded and have an inner diameter that forms a female connector that is configured to removably receive a male connector defined by an outer diameter of a snap connector 106 of one of the links. In an example embodiment, an inner diameter the ring connectors 104 is about 5.3 mm or in a range from about 5.2 mm to about 5.4 mm and/or within a range from about 2 mm to about 10 mm. In one embodiment, the perimeter (103, 103', 103", 103''') defines an interior area (111, 111', 111", 111''') within the plate. In an example embodiment, the width 107 of the perimeter is about 2.5 mm or in a range from about 1.7 mm to about 2.7 mm and/or within a range from about 1 mm to about 3 mm. In one embodiment, the perimeter (103, 103', 103", 103''') is a rectangular perimeter. In other embodiments, the perimeter is non-rectangular (e.g. concave, oval, etc.). In some embodiments, the ring connectors 104 are provided at one or more corners of the rectangular perimeter of the plate and/or the terminals 102 are provided along a side of the rectangular perimeter between the corners. In other embodiments, the terminals 102 are provided at one or more corners and/or one or more ring connectors 104 are provided along a side of the perimeter between one or more corners. In still other embodiments, the terminals 102 are provided at the corners and along the side of the perimeter between the corners and excludes ring connectors 104 (e.g. plate 110"", plate 110""') of FIGS. 1L and 1M).

In an embodiment, the system 100 includes a first plate 110 with a first rectangular perimeter 103 defined by a first width and a first length (e.g. 13 mm×50 mm) where the first width is measured between the centers of two ring connectors 104 at the corners of the plate 110 along a width dimension (e.g. shorter rectangular dimension of the plate) of the first plate 110 and the first length is measured between the centers of two ring connectors 104 at the corners of the plate 110 along a length dimension (e.g. longer rectangular dimension of the plate) of the plate 110. The first plate 110 includes the ring connector 104 at each of the four corners and a pair of terminals 102 along each side of the perimeter 103. In an example embodiment, the first plate 110 also includes a plurality of joints (105a, 105b, 105c) that connect opposite sides of the rectangular perimeter 103. In an example embodiment, each joint 105 has a cross-sectional area that is less than or equal to a maximum cross-sectional area (e.g. a vertical height of about 1.6 or in a range from about 1.3 mm to about 1.9 mm and a width of about 2.4 mm or in a range from about 2 mm to about 3 mm) capable of being cut with a pair of standard plate cutters, as discussed in the method below. In an embodiment, the pair of terminals 102 are positioned on opposite sides of the intermediate joint 105b at each side of the perimeter 103. In an example embodiment, the intermediate joint 105b divides the interior area 111 into a pair of interior areas 111a, 111b.

In another embodiment, the system 100 includes a second plate 110' with a second rectangular perimeter 103" defined by a second width and a second length (e.g. 13 mm×55 mm). The second width and second length of the second plate 110' are measured in a similar way as the first width and the first length of the first plate 110. In the example embodiment, the first length of the first plate 110 is less than the second length of the second plate 110' and/or the first width of the first plate 110 is about equal to the second width of the second plate 110'. In other embodiments, the first width is not equal to the second width. Additionally, in one embodiment, the second plate 110' includes a second terminal 102 adjacent each corner of the rectangular perimeter 103' in addition to the second terminal 102 adjacent to the intermediate link 105b. Additionally, in another embodiment, the second plate 110' includes terminals and ring connectors 102, 104 on opposite sides of the intermediate joint 105b and on each side of the second plate 110'. In yet another embodiment, the first plate 110 can include terminals and ring connectors 102, 104 on opposite sides of the intermediate joint 105b rather than the pair of terminals 102 on opposite sides of the intermediate joint 105b as depicted in FIG. 1A.

In yet another embodiment, the system 100 includes a third plate 110" that is similar to the second plate 110' but without the intermediate joint 105b and terminals 102 on either side of the intermediate joint 105b. Additionally, in one embodiment, the third plate 110" is defined by a third width and third length (e.g. 13 mm×25 mm). The third width and third length of the third plate 110" are measured in a similar way as the first width and the first length of the first plate 110. In an example embodiment, the third length is less than the first length of the first plate 110 and the second length of the second plate 110'. In another example embodiment, the third width is about equal to the first width and the second width.

In yet another embodiment, the system 100 includes a fourth plate 110" that includes the ring connectors 104 at each corner of the rectangular perimeter 103" but excludes terminals 102 and the intermediate link 105b. Additionally, in one embodiment, the fourth plate 110''' is defined by a fourth width and fourth length (e.g. 13 mm×20 mm). In an example embodiment, the fourth length is less than the first length of the first plate 110 and the second length of the second plate 110' and the third length of the third plate 110". In another example embodiment, the fourth width is about equal to the first width, the second width and the third width. The numerical dimensions discussed herein and depicted in FIG. 1A are merely one example of the dimensions of the plates and the length and width of the plates can be adjusted to be any dimension, based on characteristics of the anatomy of the patient, in order to accommodate the dimension of the bone at the fracture, as discussed in the method below. In an example embodiment, the width of the plates is about 13 mm or in a range from about 10 mm to about 16 mm and the length of the plates is in a range from about 15 mm to about 75 mm. The length and width of the plates is measured as discussed above with respect to the first length and first width of the first plate 110. Other embodiments not shown may include terminals 102 and/or ring connectors 104 at various locations along the perimeter.

In an embodiment, the system 100 includes a fifth plate 110"" (FIG. 1L) and sixth plate 110""' (FIG. 1M) that shares some features of the plates (110, 110', 110", 110''') with the exception of the features discussed herein. In an embodiment, unlike the plates of FIG. 1A, the plates 110"", 110""' feature terminals 102 and exclude ring connectors 104. However, in other embodiments, one or more of the openings of the plates 110"", 110""' can be ring connectors 104. In one embodiment, the fifth plate 110" includes four corner terminals 102e, 102f, 102g, 102h that define a rectangular interior area 111. Additionally, four distal terminals 102a, 102b, 102c, 102d are spaced apart from the respective corner terminals 102e, 102f, 102g, 102h by a respective groove 133. Additionally, in an embodiment, the groove 133 and distal terminal 102a, 102b, 102c, 102d form a non-zero and non-orthogonal angle (e.g. about 45 degrees or in a range from about 30 degrees to about 60 degrees) relative to a side of the plate 110'''' defining the rectangular interior area 111. In some embodiments, the thickness of the plates 110'''', 110''''' is about 2.2 mm or in a range from about 1 mm to about 3 mm. In another embodiment, a groove 133' is provided between adjacent corner terminals 102e, 102f, 102g, 102g. In an example embodiment, the grooves 133, 133' are used to wrap lash wire over the plate to maintain a location of the plate and/or as a bending point to improve mating of the plate with the patient surface anatomy and topology of the bone. The sixth plate 110''''' is similar to the fifth plate 110'''' with the exception that the sixth plate 110''''' further includes interior terminals 102i, 102j, 102k, 102l and a joint 105 to divide a first interior area 111a from a second interior area 111b. Each terminal 102 of the plates 110'''', 110''''' need receive a fastener 117, 119 during step 412 of the method 400.

In an embodiment, the modular system 100 also includes a link (120, 124, 126, 128, 130, 131, 132, 134, 136, 137, 138) that has one or more openings including one or more terminals 102, ring connectors 104 and/or snap connectors 106 adjacent the one or more openings. In an embodiment, one or more snap connectors 106 is a male connector with an outer diameter configured to be removably received by a female connector along an inner diameter of the ring connector 104 of one of the plates or a second link of the system 100. Upon the male connector of the snap connector 106 of a first link of the system 100 being removably received in the ring connector 104 of the plate or the second link of the system 100, the first link is rotatably received within the ring connector 104 of the plate or the second link. In one embodiment, the terminals 102, ring connectors 104 and/or snap connectors 106 of each link are provided along a linear axis 121 (e.g. see link 120 in FIG. 1A) defining the link 120. In other embodiments, the axis is non-linear (e.g. arcuate axis), such as an arcuate axis with a predetermined radius of curvature. In some embodiments, the terminals 102, ring connectors 104 and/or snap connectors 106 are provided along a pair of linear axes 121a, 121b that define the link 138, 138' (e.g. wye link 138, 138', where the axes 121a, 121b intersect at the snap connector 106).

Figure 1F:
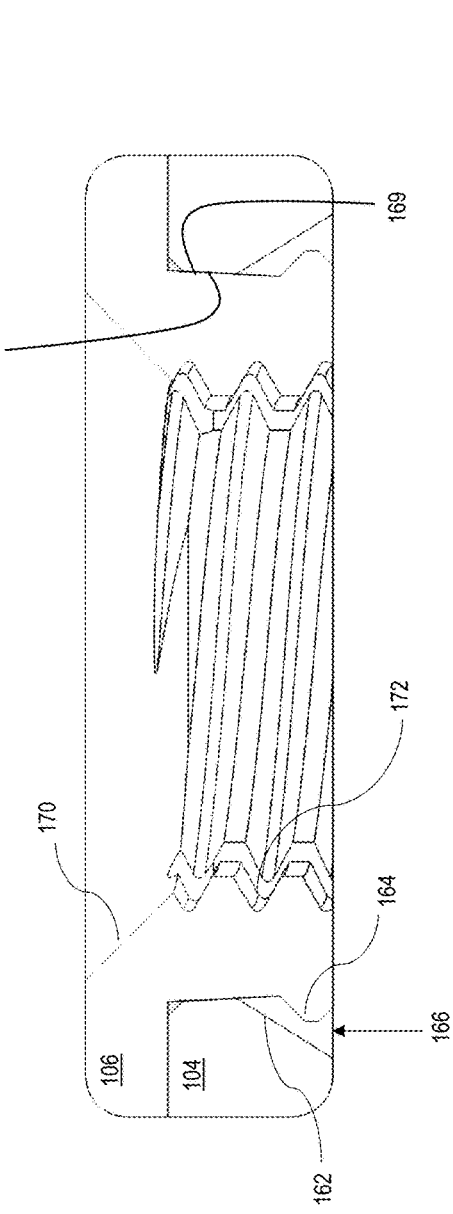
FIGS. 1F and 1G are images that illustrate example cross-sectional side views of a male connector and female connector of the modular system of FIGS. 1A-1B, according to an embodiment.

FIG. 1F is an image that illustrates an example of a side view of an interface 160 between a male connector of the snap connector 106 and female connector of the ring connector 104 of the modular system of FIGS. 1A-1B, according to an embodiment. In an embodiment, the inner diameter of the snap connector 106 defines a conical surface 170 that extends to an internal threaded hole 172 to receive an external threaded fastener (117, 119) and an outer diameter of the snap connector 106 includes a tapered portion 168 and a pair of tabs 164 that are configured to be inwardly deflected. In an embodiment, the inner diameter of the ring connector 104 is the female connector with a tapered portion 169 and a chamfer 162. In an embodiment, the tapered portion 168 and/or the tapered portion 169 has a taper of about 6 degrees or in a range from about 2 degrees to about 14 degrees. Upon engagement of the male connector with the female connector, the tabs 164 deflect inward around the tapered portion 169 of the inner diameter of the ring connector 104 and snap back to their natural position and the tapered portion 168 of the outer diameter of the snap connector 106 rotatably engages the tapered portion 169 of the inner diameter of the ring connector 104. In an embodiment, the tabs 164 are spaced apart from the chamfer 162 by a recess 166 (e.g. about 0.63 mm or in a range from about 0.6 mm to about 0.68 mm and/or in a range from about 0.4 mm to about 0.9 mm). In an embodiment, a height of the plates and/or links is less than or equal to a threshold height (e.g. about 2.2 mm) where the threshold height is based on a dimension between the bone and an inside surface of the skin of the subject. This advantageously ensures that the profile of the structure assembled with the modular system 100 (e.g. the height) does not exceed the threshold height so that the assembled structure does not protrude into the skin of the subject. In an example embodiment, the threshold height is about 2.2 mm for the chest with the sternum bone. In an additional embodiment, the height of the combined ring connectors 104 and snap connectors 106 of the engaged male and female connectors is not greater than the threshold height.

Figure 1G:
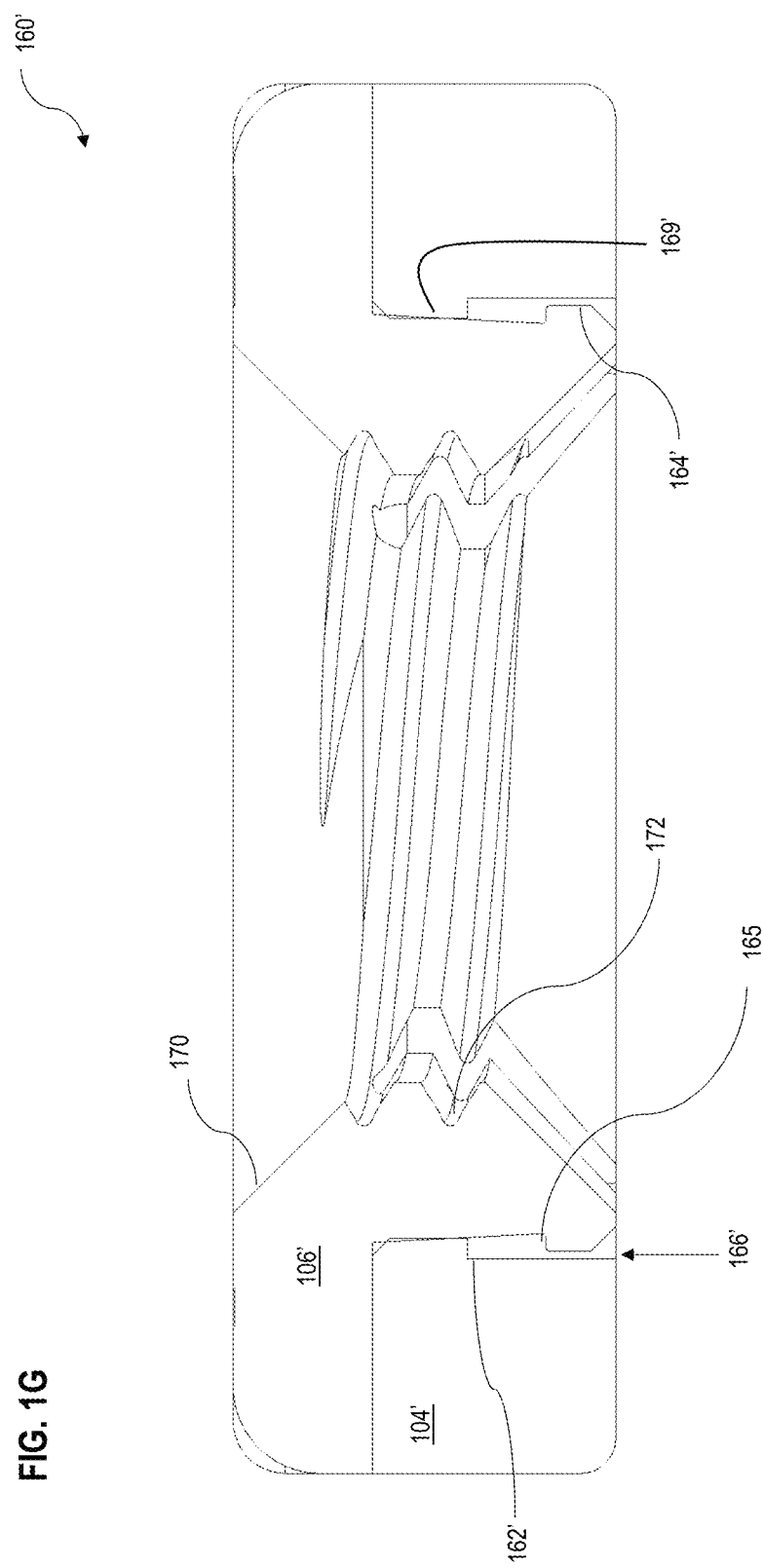
Figure 1H:
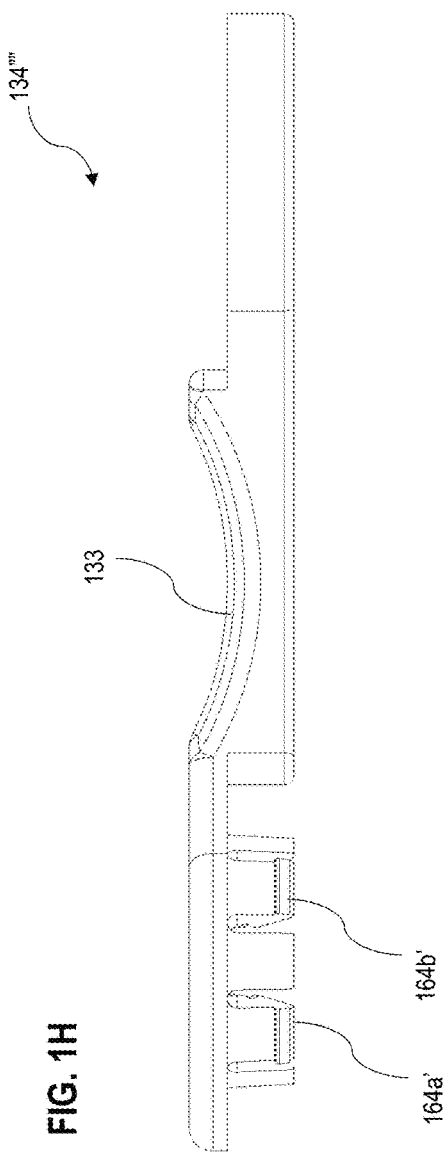
FIGS. 1H through 1K are images that illustrate an example of a link for use in the modular system of FIGS. 1A and 1B, according to an embodiment.

In an embodiment, the interface between the male connector of the snap connector and the female connector of the ring connector is not limited to the structural arrangement of FIG. 1F. In another embodiment, an interface 160' is formed between a male connector of a snap connector 106' and a female connector of the ring connector 104'. The interface 160' can be used instead of the interface 160 for any snap connector and ring connector attachment of the modular system 100. FIG. 1G is an image that illustrates an example of a side view of a male connector of the snap connector 106' and female connector of the ring connector 104' of the modular system of FIGS. 1A-1B, according to an embodiment. In an embodiment, the inner diameter of the snap connector 106' defines the internal threaded hole 172 to receive the external threaded fastener (117, 119) and the outer diameter of the snap connector 106 includes tabs 164' that feature a tapered portion that are configured to be inwardly deflected (e.g. different than the tabs 164 of FIG. 1F). In an embodiment, the inner diameter of the ring connector 104' is the female connector with a tapered portion 169' (e.g. that is longer than the tapered portion 169 and thus engages the tabs 164' over a longer distance than the tabs 164 engaging the threaded portion 169 in FIG. 1F) and a counterbore 162' (e.g. an orthogonal step). In an example embodiment, the inner diameter of the ring connector 104' transitions at the counterbore 162' from a first value (e.g. about 0.45 mm or in a range from about 0.35 mm to about 0.55 mm) to a second value greater than the first value (e.g. about 0.85 mm or in a range from about 0.7 mm to about 1 mm). In an embodiment, the tapered portion 169' has a taper of about 6 degrees or in a range from about 2 degrees to about 14 degrees. Upon engagement of the male connector with the female connector, the tapered portion of the tabs 164' maintain engagement with the tapered portion 169' of the ring connector 104' over a sufficient distance before the tabs 164' deflect inward at the counterbore 162' to their natural position and the outer diameter of the snap connector 106' rotatably engages the tapered portion 169' of the inner diameter of the ring connector 104'. In an embodiment, the tabs 164' are spaced apart from the counterbore 162' by a recess 166' (e.g. less than the recess 166). In an embodiment, a height of the plates and/or links is less than or equal to a threshold height (e.g. about 3 mm) where the threshold height is based on a dimension between the bone and an inside surface of the skin of the subject. The counterbore 162' advantageously secures the snap connector 106' within the ring connector 104' since the snap connector 106' features an orthogonal step 165 (e.g. different than the tab 164 of FIG. 1F with arcuate surface) so that the snap connector 106' cannot be easily removed from the ring connector 104' (e.g. the counterbore 162' provides a secure barrier to prevent passage of the orthogonal step 165).

The first link with the snap connector 106, 106' can be rotated relative to the plate or second link with the ring connector 104, 104', until the first link has a desired orientation relative to the plate or second link, after which the threaded fastener 117 is secured through the threaded hole 172 and into bone below the plate or second link, which rotatably fixes the tapered portions 168, 169 or 168', 169' (e.g. a taper lock) of the first link with respect to the plate or second link. In another embodiment, the plates can include one or more snap connectors 106, 106' so that the plates can matingly engage with a female connector (e.g. ring connector 104, 104') of another plate or a link. Although a specific male-female connector and mating arrangement is discussed herein and depicted in FIG. 1F and FIG. 1G, these are merely examples of mating arrangements between the ring connector 104, 104' of the first link and the snap connector 106, 106' of the plate or second link and the present invention includes any mating connector arrangement (e.g. a crimp or grommet arrangement) appreciated by one of ordinary skill in the art. Additionally, in other embodiments the arrangement of the ring connector 104, 104' and snap connector 106, 106' in the system can be reversed so that the ring connector 104, 104' is moved down over the snap connector 106,106' (e.g. an inverted version of FIG. 1F or FIG. 1G).

In an embodiment, the links include a first link 130 that includes a single snap connector 106, 106' that defines the male connector. In one embodiment, the first link 130 is advantageously provided so that it can be connected to the ring connector 104, 104' of a plate or second link, in order that the fastener 117, 119 can be threaded into the bone (e.g. through the threaded hole 172 of the opening 106) through the ring connector 104, 104'. In an example embodiment, the first link 130 can be used when the ring connector 104, 104' of the plate or second link needs to be secured to the bone, but no further coverage is necessary beyond the ring connector 104, 104'.

In an embodiment, the links include a second link 132, 132', 132", 132'" that includes a snap connector 106, 106' and terminal 102 that are spaced apart. In one embodiment, the second link 132 features the snap connector 106, 106' and terminal 102 having a first spacing (e.g. 8 mm); the second link 132' features the snap connector 106, 106' and terminal 102 having a second spacing (e.g. 10 mm) greater than the first spacing; the second link 132" features the snap connector 106, 106' and terminal 102 having a third spacing (e.g. 12 mm) greater than the second spacing; and the second link 132'" features the snap connector 106, 106' and terminal 102 having a fourth spacing (e.g. 16 mm) greater than the third spacing. In one example embodiment, the second link can be used to advantageously provide two threaded holes 172 and thus accommodate the fastening of two threaded fasteners 117, 119 to the bone in a vicinity of the ring connector 104, 104', to more rigidly secure the assembled structure to the bone at the bone fragment.

In another embodiment, in one embodiment, the second link 132' includes a groove 133 provided between the snap connector 106, 106' and terminal 102 that is sized to receive a band or wire that is wrapped around the bone fracture (e.g. in a direction perpendicular to the direction of the fracture). In an example embodiment, the depth of the groove 133 is greater than or equal to a height of the band or wire in the groove 133 so that the band or wire does not extend above the profile of the link 132 and/or the width of the groove 133 is greater than or equal to a width of the band or wire in the groove 133 so that the band or wire fits within the groove 133. In another embodiment, in one embodiment, the second link 132" includes a groove 133' provided between the snap connector 106, 106' and terminal 102 that is sized to receive a band or wire that is wrapped around the bone fracture. In an example embodiment, the depth of the groove 133' is greater than or equal to a height of the band or wire in the groove 133' so that the band or wire does not extend above the profile of the link 132" and/or a width of the groove 133' is greater than or equal to a width of the band or wire in the groove 133' so that the band or wire fits within the groove 133'. In one example embodiment, the depth of the groove is the same for all plates and/or links. In another embodiment, in one embodiment, the second link 132'" includes a groove 133" provided between the snap connector 106, 106' and terminal 102 that is sized to receive a band (e.g. elastic band) that is wrapped around the bone fracture. In an example embodiment, the depth of the groove 133" is greater than or equal to a height of the band in the groove 133" so that the band does not extend above the profile of the link 132'" and/or the width of the groove 133" is greater than or equal to a width of the band in the groove 133" so that the band fits within the groove 133". In addition to wrapping wire around the modular system and along the groove 133, 133', 133", the groove provides a means to manipulate the orientation of the link and/or plate of the modular system to accommodate the surface of the patient anatomy (e.g. bone).

In an embodiment, the links include a third link 134, 134', 134", 134'" that are similar to the second links discussed above, with the exception that the third link includes a snap connector 106, 106' separated from a ring connector 104, 104'. In one embodiment, the third link can be used to advantageously secure the male connector defined by the snap connector 106, 106' in a female connector defined by the ring connector 104, 104' in a plate or second link, after which the ring connector 104, 104' of the third link can be subsequently used to engage with a snap connector 106, 106' of a subsequent plate or link of the system 100. Similarly, the links include a fourth link 136, 136', 136" that are similar to the second links 132', 132", 132'" with the exception that the fourth link includes a pair of spaced apart ring connectors 104, 104'. In one embodiment, the fourth link can be used to advantageously engage a snap connector 106, 106' of a first link in a first ring connector 104, 104' of the fourth link and a snap connector 106, 106' of a second link in a second ring connector 104, 104' of the fourth link, to permit two links to be secured to the pair of spaced apart ring connectors 104, 104'. Additionally, the links include a fifth link 131', 131", 131'" that are similar to the second links 132', 132", 132'" with the exception that the fifth link includes a pair of spaced apart snap connectors 106a, 106b.

Figure 1I:
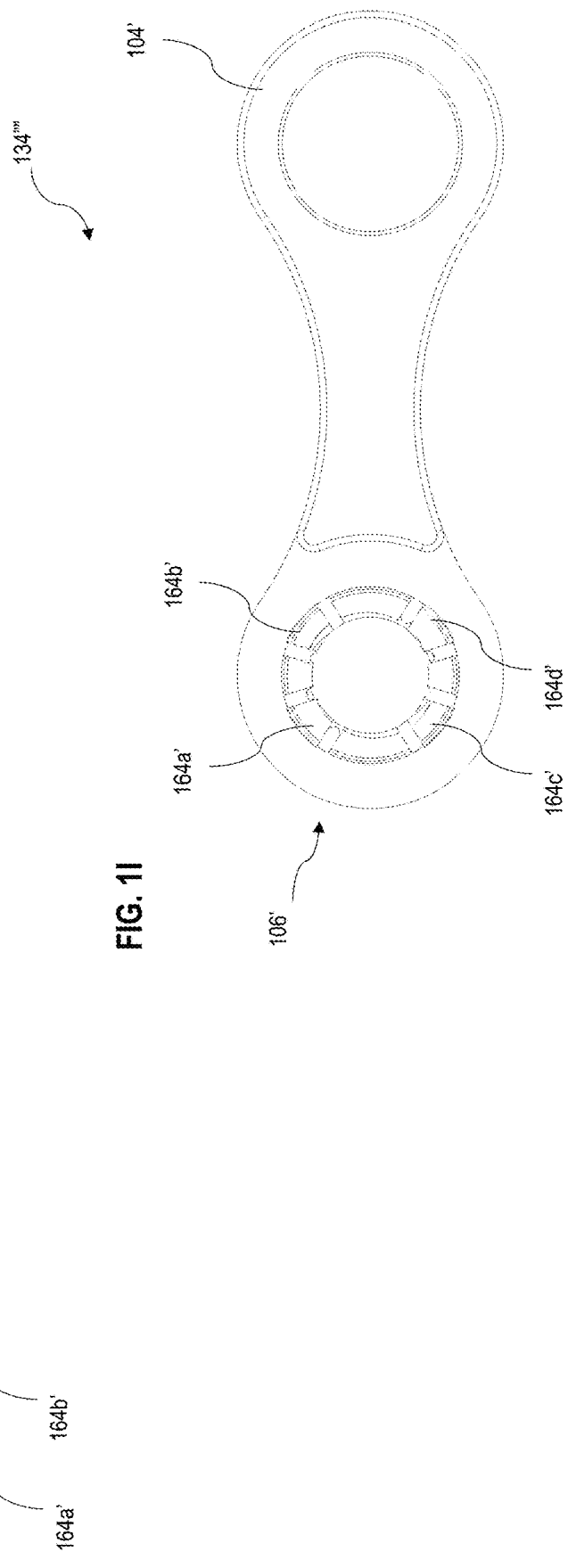
Figure 1J:
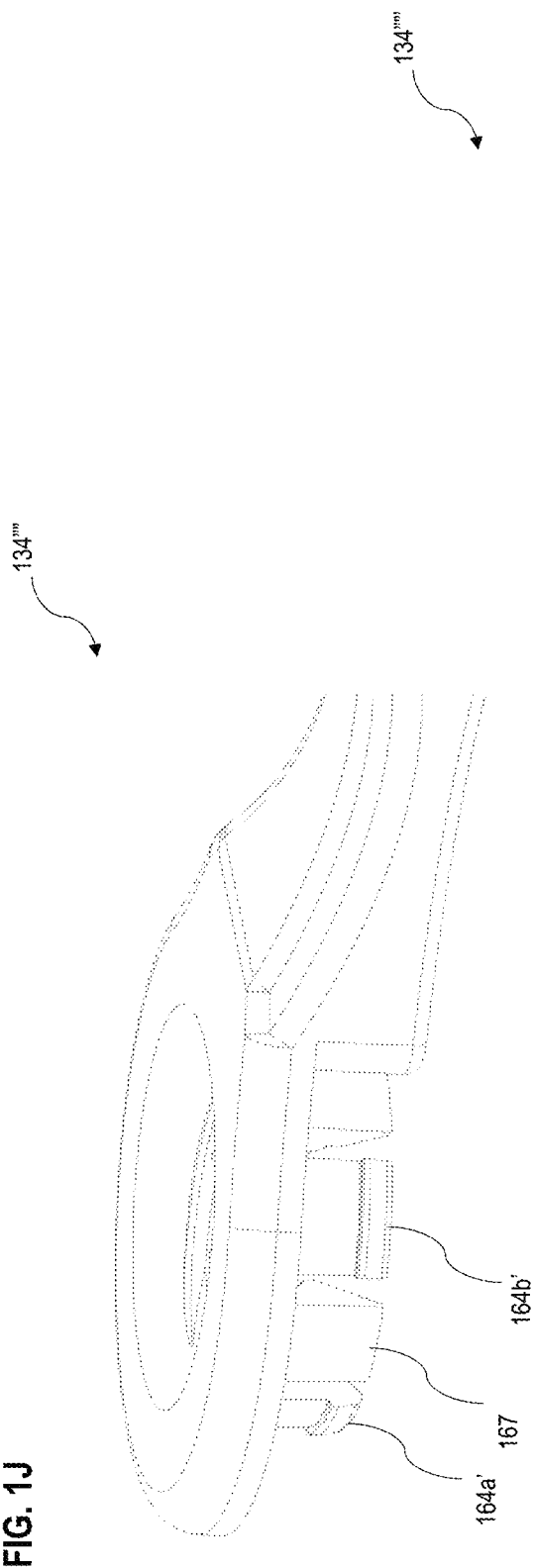
Figure 1K:
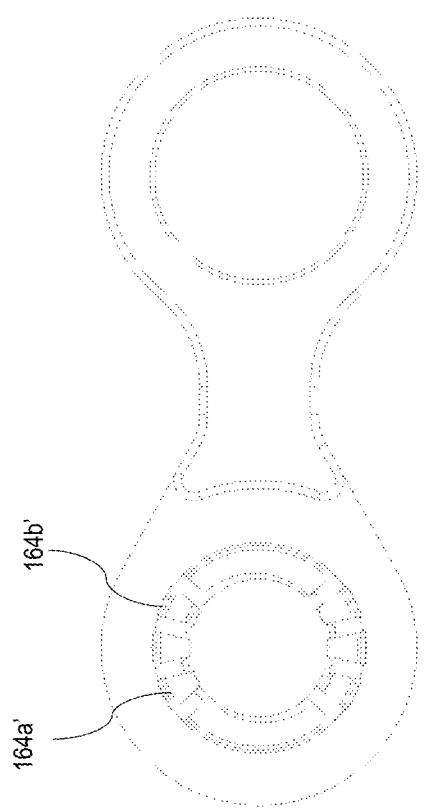
Figure 1M:
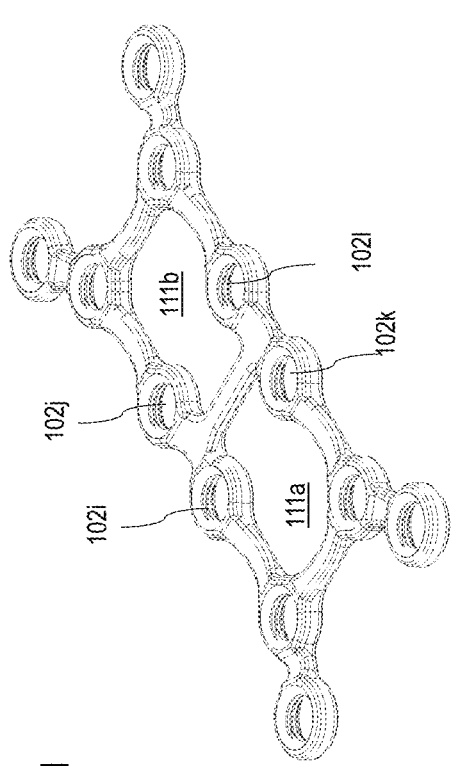
FIGS. 1L and 1M are images that illustrate an example of plates for use in the modular system of FIGS. 1A and 1B, according to an embodiment.
Figure 1L:
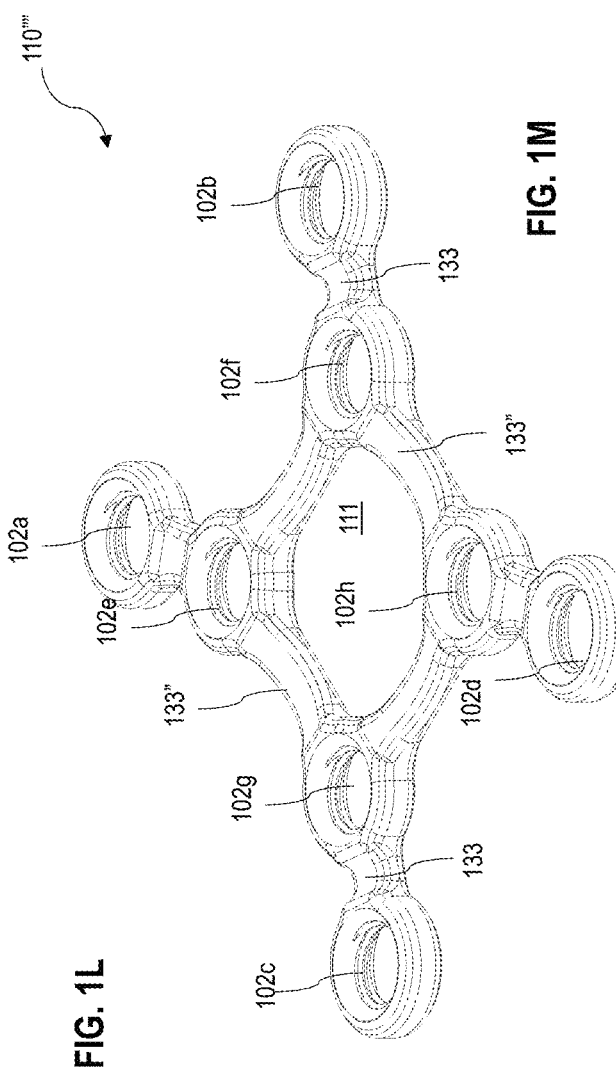

FIGS. 1H through 1K are images that illustrate an example of a link 134"" for use in the modular system of FIGS. 1A and 1B, according to an embodiment. Unlike the links 134, 134', 134", 134'", the link 134"" features more than two tabs 164' about a circumference of the snap connector 106, 106'. As shown in FIG. 1I, the link 134"" features four tabs 164a', 164b', 164c', 164d' that are circumferentially spaced (e.g. by collar 167, see FIG. 1J) around the snap connector 106, 106'. In one example embodiment, an arc length of the tabs 164a', 164b', 164c', 164d' is less than an arc length of the tabs 164 of the links 134, 134', 134", 134'" and thus the tabs 164a', 164b', 164c', 164d' are more flexible and thus deflect easier around the tapered inner surface 169' of the ring connector 104'. Although FIGS. 1H through 1K depict four tabs 164' circumferentially spaced around the snap connector 106' (e.g. 2 o'clock, 4 o'clock, 8 o'clock and 10 o'clock positions), in other embodiments, more or less than four tabs 164' may be circumferentially spaced about the snap connector 106' (e.g. 6 tabs 164' such as at 2 o'clock, 3 o'clock, 4 o'clock, 8 o'clock, 9 o'clock and 10 o'clock positions). In an example embodiment, an arc length of the tabs 164' (e.g. at the most distal end of the collar) is about 1 mm or in a range from about 0.5 mm to about 1.5 mm. Although the tabs 164' could be formed with smaller arc length, the inventors of the present invention recognized that they have an increased risk of snapping/breaking upon deflection around the tapered inner diameter 169' of the ring connector 104'. Additionally, the inventors of the present invention recognized that the arc length of the tabs 164' should be sufficiently large that they secure and maintain the snap connector 106' within the ring connector 104'. Accordingly, the inventors of the present invention utilized arc lengths for the tabs 164' within the above cited range. However, the arc length of the tabs 164' is not limited to any particular range and the above range is merely one example of a dimensional range for the tab arc length. Although the above discussion of the tabs 164' was in regard to the link 134'''', the tabs 164' of any snap connector 104' used in the modular system 100 can share these features.

In an embodiment, the links include a sixth link 137 with multiple terminals 102, 102' (e.g. four) that are closely spaced and a single snap connector 106, 106' that is spaced apart from the multiple terminals 102, 102'. In an example embodiment, the single snap connector 106, 106' is spaced apart from the multiple terminals 102, 102' with the groove 133'. In an example embodiment, the sixth link 137 includes the single snap connector 106, 106' that can be matingly engaged with a ring connector 104, 104' of a plate or second link, after which fasteners can be threaded through one or more of the multiple terminals 102, 102', to advantageously provide multiple fasteners into the bone and thus increase the rigid connection between the assembly structure with the modular system 100 and the bone including the fracture.

In an embodiment, the links include a seventh link 138, 138', 138'' that includes a triangular arrangement of openings defined by a pair of linear axes 121a, 121b that intersect at a snap connector 106, 106'. In another embodiment, the sixth link could be arranged with the axes 121a, 121b intersecting at a ring connector 104, 104'. In one embodiment, the seventh link 138 is a wye link including one snap connector 106a, 106a' and a pair of terminals 102a, 102b. In an example embodiment, the seventh link 138 includes the single snap connector 106a, 106a' spaced apart from a pair of terminals 102a, 102b by a groove 139 that is similar to the groove 133'. In another embodiment, the seventh link 138' is a wye link including one snap connector 106a, 106a' and a pair of ring connectors (104a, 104b),(104a', 104b'). In an example embodiment, the snap connector 106a, 106a' and pair of ring connectors (104a, 104b)(104a', 104b') are spaced apart by the groove 139. In one embodiment, either or both seventh links 138, 138' can be used to matingly engage the male connector at the apex snap connector 106a, 106a' with a female connector at a ring connector 104, 104' of a plate or second link, after which multiple fasteners can be secured through the other two terminals 102a, 102b (e.g. link 138) or additional links can be matingly secured to one or both of the two ring connectors (104a, 104b)(104a', 104b') (e.g. link 138').

Figure 1P:
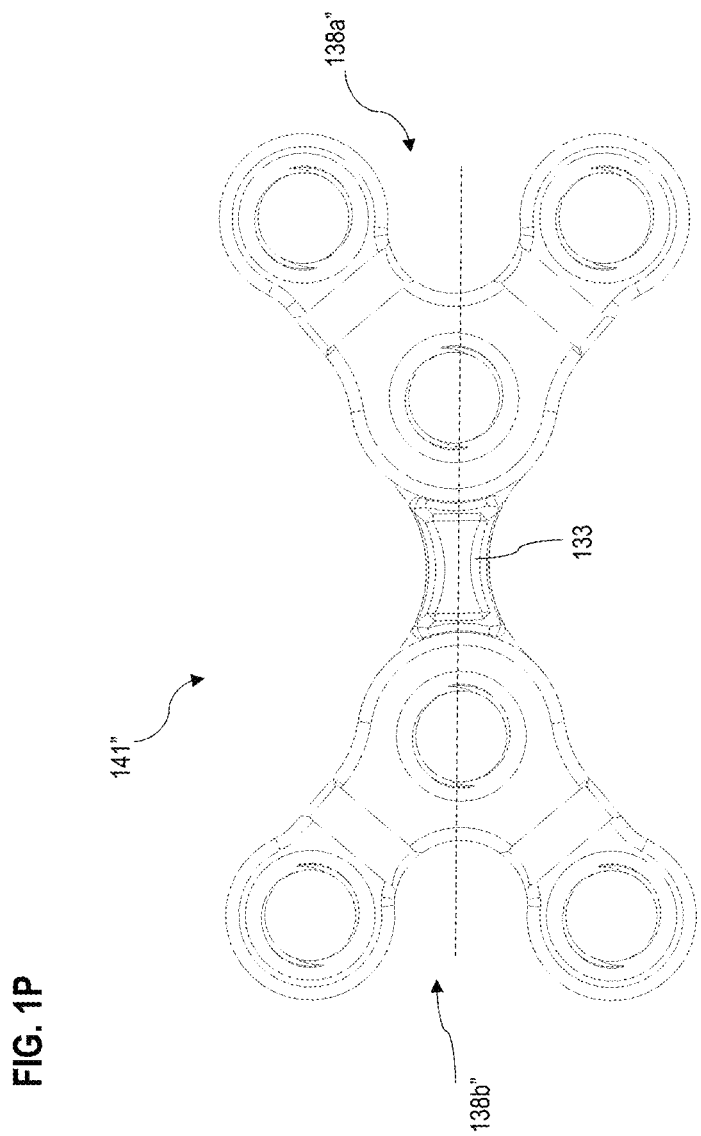

In still other embodiments, the seventh link 138'' includes a triangular arrangement of openings that feature a snap connector 106' and a pair of terminals 102. FIGS. 1N through 1P are images that illustrate an example of an eighth link 141, 141', 141'' for use in the modular system of FIGS. 1A and 1B, according to an embodiment. In an embodiment, the eighth links 141, 141', 141'' each feature two seventh links 138a'', 138b'' (e.g. a triangular arrangement of openings that feature the snap connector 106, 106' and a pair of terminals 102) where the snap connector 106, 106' of the seventh links 138a'', 138b'' are connected to ring connectors 104, 104' of the fourth link 136, 136', 136''. In an embodiment, the eighth link 141 provides a groove 133' between the snap connectors 106a, 106b and a groove 133 between each terminal 102 and the snap connector 106a, 106b. The grooves 133, 133' can be used for similar purposes as the grooves discussed above (e.g. to wrap wire around the link and/or to manipulate the orientation of the link so to accommodate surface anatomy of the patient, e.g. bone surface). In some embodiments, the eighth link 141 is designed so that the angle 143 between a central axis 147a of the first seventh link 138a'' and a central axis 147b of the second seventh link 138b'' can be chosen among one or more values (e.g. about 65 degrees, about 80 degrees, about 90 degrees, about 120 degrees, etc.). In an embodiment, the eighth link 141' is similar to the eighth link 141 with the exception that the axes 147a, 147b are about parallel and/or the angle 145 that a line connecting the snap connectors 106a, 106b makes with the axes 147a, 147b is about 45 degrees or in a range from about 30 degrees to about 60 degrees.

In an embodiment, the links include a ninth link 120 that is similar to the sixth link 137 but also includes a ring connector 104, 104' at an opposite end of the multiple terminals 102 from the single snap connector 106, 106'. In one embodiment, the single ring connector 104, 104' is spaced apart from the multiple snap connectors 106, 106' with the groove 133'.

In an embodiment, the links include a tenth link 124 that is similar to the ninth link 120 except instead of having a single snap connector 106, 106' at one end and a single ring connector 104, 104' at an opposite end and multiple terminals 102 therebetween (e.g. four), the tenth link 124 has a single ring connector 104, 104' at each opposite end of the link. In another embodiment, unlike the ninth link 120, in some embodiments there is no groove 133' between the ring connector 104, 104' at each end of the link and an adjacent terminal 102.

In an embodiment, the links include an eleventh link 126 that is similar to the tenth link 124 except instead of having a pair of spaced apart terminals 102 between the opposite ends of the link (e.g. where each end includes a ring connector 104, 104' at the tip of the link and a terminal 102 positioned adjacent and inward of the ring connector 104, 104') the eleventh link 126 includes an adjacent ring connector 104, 104' and terminal 102 positioned along the length of the link between the opposite ends of the link.

The twelfth link 128 is similar to the eleventh link 126 except an adjacent pair of terminals 102 are provided along the length of the link between the opposite ends of the link.

In an embodiment, FIG. 1D depicts an interconnection 125 of two of the third links 134'' that are snapped together. In one embodiment, the male connector of the snap connector 106a of one third link 134'' matingly engages the female connector of inner diameter of the ring connector 104 of a second third link 134''.

FIG. 1C is an image that illustrates an example of a front view of a first link (e.g. second 132) rotatably coupled to a second link (e.g. tenth link 124) of the modular system 100 of FIGS. 1A-1B, according to an embodiment. As depicted in FIG. 1C, in one embodiment, the male connector of the snap connector 106, 106' of the second link 132 is matingly engaged by the female connector defined by the inner diameter of the ring connector 104, 104' at one end of the tenth link 124. The second link 132 is rotatably received in the ring connector 104, 104' at the end of the tenth link 124. In an embodiment, the second link 132 is rotatable from a first orientation 140a to a second orientation 140b relative to the tenth link 124. In one embodiment, in the second orientation 140b the second link 132 forms an angle 142 (e.g. about 113 degrees) with the tenth link 124. In an example embodiment, the angle between the second link 132 and the tenth link 124 is adjusted based on one or more characteristics of an anatomy of a patient including the bone with the fracture, e.g. a dimension of the bone, an angle that a second bone forms with the first bone, etc. After the second link 132 is rotated to a desired orientation (e.g. orientation 140b) with the tenth link 124, the desired orientation can be fixed by securing one or more fasteners 117, 119 through the threaded hole 172 of the snap connector 106, 106' rotatably received within the ring connector 104, 104' of the tenth link 124.

As further depicted in FIG. 1C, in one embodiment, the male connector of the snap connector 106, 106' of the second link 132 is matingly engaged by the female connector defined by the inner diameter of the ring connector 104, 104' along an interior of the eleventh link 126. The second link 132 is rotatably received in the ring connector 104, 104' along the interior of the eleventh link 126. In an embodiment, the second link 132 is rotatable from a first orientation 144a to a second orientation 144b relative to the eleventh link 126. In one embodiment, in the first orientation 144a the second link 132 forms an angle 146a (e.g. about 37 degrees) with the eleventh link 126 and in the second orientation 144b the second link 132 forms an angle 146b (e.g. about 27 degrees) with the eleventh link 126. In an example embodiment, the angle between the second link 132 and the eleventh link 126 is adjusted based on one or more characteristics of an anatomy of a patient including the bone with the fracture, e.g. a dimension of the bone, an angle that a second bone forms with the first bone, etc. After the second link 132 is rotated to a desired orientation (e.g. orientation 144b) with the eleventh link 126, the desired orientation can be fixed by securing one or more fasteners 117, 119 through the threaded hole 172 of the snap connector 106, 106' rotatably received within the ring connector 104, 104' of the eleventh link 126. The technique discussed above with respect to FIG. 1C can be employed for rotatably receiving a link to any plate or second link of the modular system 100, rotatably adjusting an orientation of the link relative to the plate or second link and rotatably fixing the link in a desired orientation relative to the plate or second link.

FIG. 1E is an image that illustrates an example of a side view of a fastener of the system of FIG. 1A, according to an embodiment. In an embodiment, the fastener 117, 119 is an externally threaded fastener with threads 150 in a base of the fastener and threads 152 adjacent a head of the fastener. In an example embodiment, the fastener is an externally threaded screw with a major diameter (e.g. about 3 mm and/or or about 3.3 mm and/or in a range from about 2 mm to about 4 mm). In another example embodiment, the length of the fastener (e.g. the externally threaded screw) is about 10 mm, 13 mm, 16 mm and/or the length is selected in a range that varies from about 8 mm to about 20 mm. In an example embodiment, the threads 150 (e.g. 2 mm thread pitch with a 60 degree self-tapping tapered tip) and the threads 152 (e.g. M4×0.5 mm dual lead threads) have one more parameters which differ from each other, such as the spacing and/or tilt angle of the threads, etc. This advantageously reduces the likelihood that the fastener 117 will unwind and loosen from the bone once it is fastened within the bone. In an example embodiment, in the event that spontaneous movement of the subject caused the threads 150 of the fastener 117 to unwind, the threads 152 adjacent the head of the fastener advantageously do not unwind due to the different parameters (e.g. spacing, angle, etc.) of the threads 152. This advantageously ensures that the fastener remains securely within the bone of the subject and keeps the fracture closed.

Figure 4:
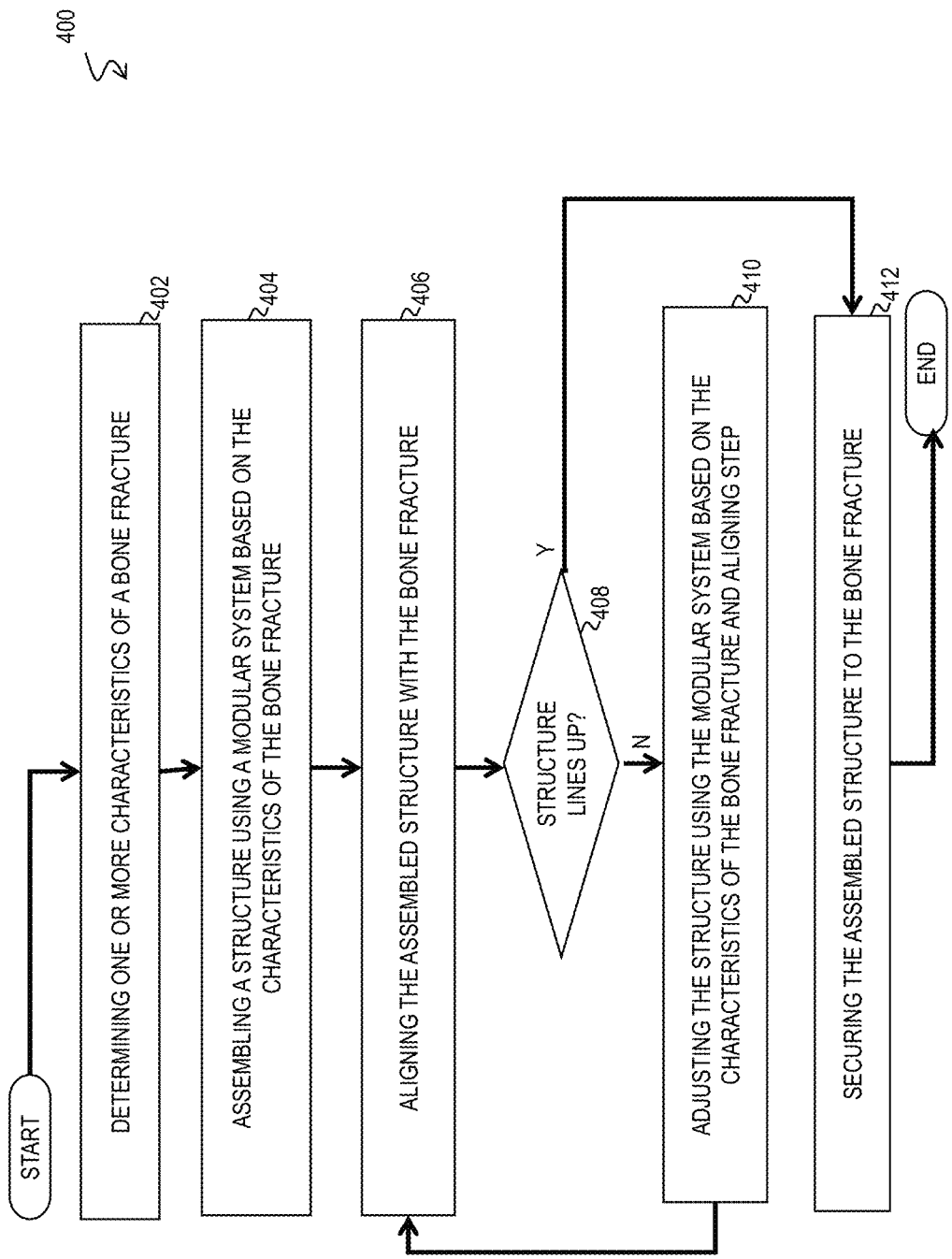
FIG. 4 is a flowchart illustrates an example of a method for assembling a structure to secure to opposite sides of a fracture in a bone, according to an embodiment.

FIG. 4 is a flowchart that illustrates an example of a method 400 for assembling a structure to secure to opposite sides of a fracture in a bone of a subject. Although steps are depicted in FIG. 4 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 402, one or more characteristics of the anatomy of the subject including the bone with the fracture is determined. In an embodiment, the characteristic determined in step 402 is a dimension of the anatomy of the subject including the bone with the fracture. In one embodiment, the characteristic is a dimension of the bone, a dimension of an adjacent bone connected or adjacent to the bone, a quality of the bone (e.g. osteoporotic quality), a quality of the adjacent bone (e.g. osteoporotic quality), and/or an angle that the adjacent angle forms with the bone.

Figure 2A:
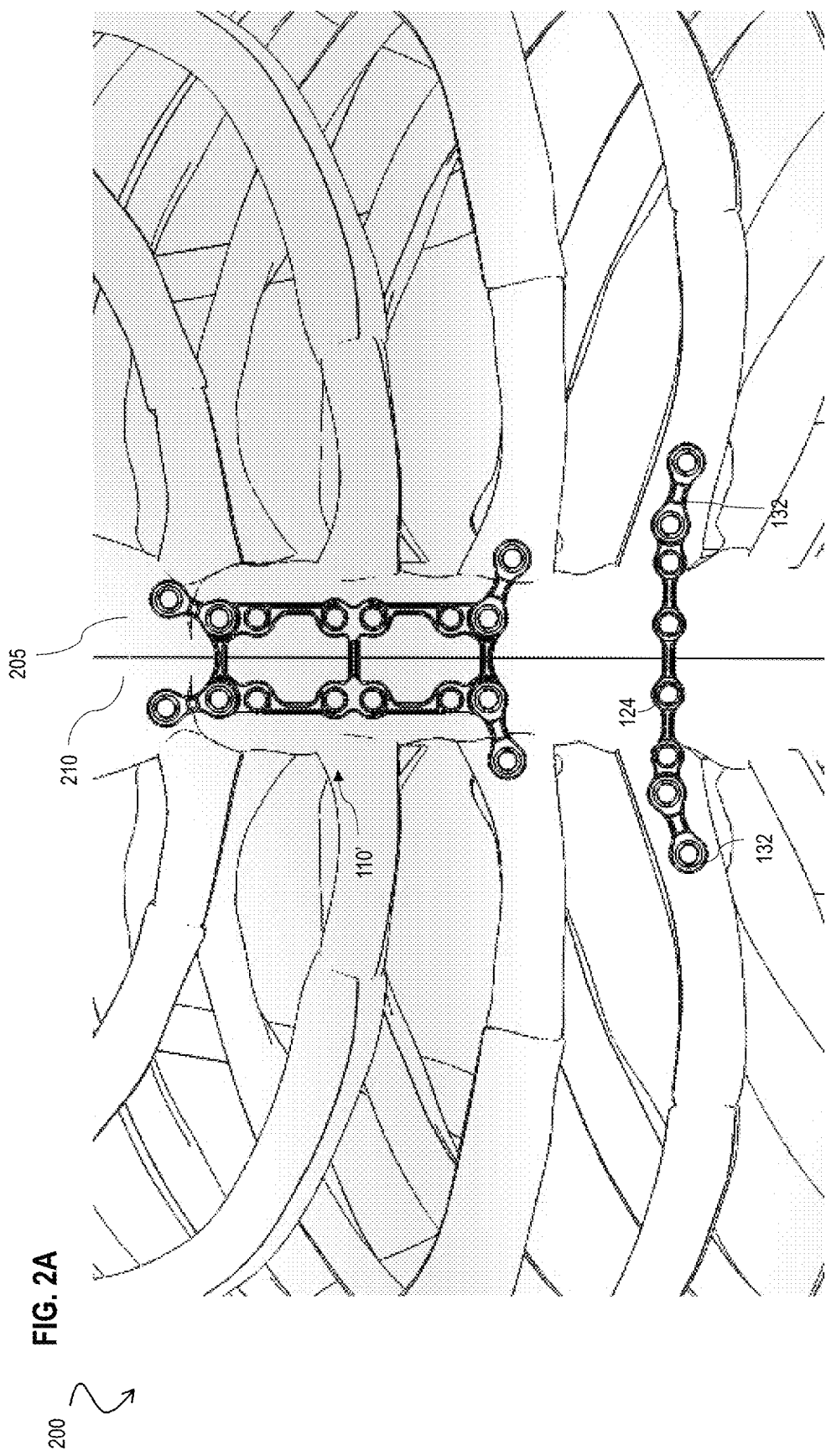
FIG. 2A is an image that illustrates a front view of a structure assembled with the modular system of FIGS. 1A-1B and aligned with a fracture in a sternum of a subject, according to an embodiment.
Figure 2B:
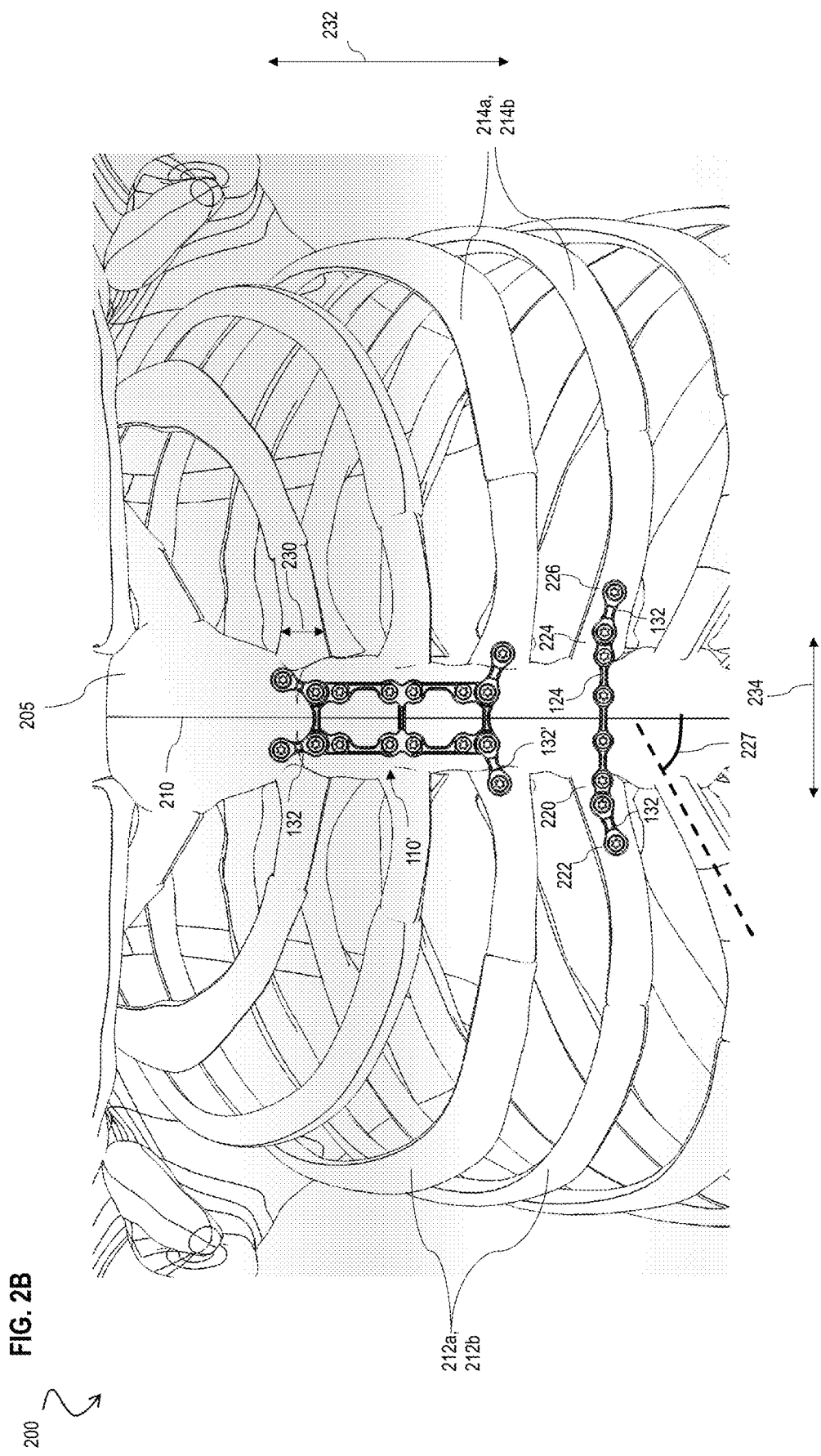
FIG. 2B is an image that illustrates an example of a front view of the structure of FIG. 2A secured to the sternum, according to an embodiment.

In an embodiment, the subject is a human and the bone is a sternum 205. FIGS. 2A-2B are images that illustrates a front view of a structure 200 assembled with the modular system 100 of FIGS. 1A-1B and aligned with a fracture 210 in a sternum 205 of a subject, according to an embodiment. In one embodiment, in step 402 the dimension that is determined includes a length and/or a width of the sternum 205 and/or a rib 212 bone that is adjacent to and connected to the sternum 205. In an example embodiment, in step 402 a length 232 along the sternum 205 and parallel to the fracture 210 is measured, e.g. between a first location and a second location where a rib 212a intersects the sternum 205. In this example embodiment, the length 232 is measured based on the distance to a rib 212a where one or more links may want to be secured due to one or more favorable characteristics of the rib 212a (e.g. dimension, bone quality, etc.). In another example embodiment, in step 402 a width 234 along the sternum 205 is measured, e.g. a distance about orthogonal to the fracture 210 and measured between the connection joints of opposite ribs 212b, 214b to the sternum 205. In this example embodiment, the width 234 may be measured in order to choose a plate or link with the appropriate width or length to fit along the width 234 of the sternum 205. Although only one length 232 and width 234 dimension along the sternum 205 is discussed and depicted in FIG. 2B, this is merely for illustrative purposes and the embodiments of the present invention can measure multiple lengths and widths along the sternum 205 in order to assist with the assembly of the structure 200. Additionally, although step 402 discusses that various characteristics including dimensions and/or angles can be determined, in some embodiments this merely means that the characteristics are visually assessed and/or visually determined and does not require any physical measurement be taken and/or recorded.

In another embodiment, in step 402 one or more angles 227 are measured between one nor more ribs 212 and the sternum 205. In an example embodiment, the angle 227 is used to determine the extent to which a link rotatably fixed to a plate or second link should be rotated to have the necessary orientation to line up with the rib. In another embodiment, in step 402 one or more dimensions of the ribs 212 are determined, such as a width 230 of one of the ribs 212 adjacent to the sternum 205. In an example embodiment, the width 230 may help to determine a width of a link to be secured to the rib and/or whether multiple links can be secured along the rib (e.g. if the width 230 exceeds a threshold). Although one angle 227 and width 230 is discussed and depicted in FIG. 2B, this is merely for illustrative purposes and the embodiments of the present invention can measure the angle 227 and/or width 230 of each rib connected to the sternum 205 and use each angle 227 in the assembly of the structure 200.

In another embodiment, in step 402 the bone quality is determined over the sternum 205 and/or one or more ribs 212. In an embodiment, in step 402 it is determined that an inner region 220, 224 of the ribs 212 adjacent a connection joint with the sternum 205 has low bone quality, so that it can be determined whether a link should be secured to that rib and/or how long of a link should be chosen to ensure that the link can extend to an outer region 222, 226 of the ribs 212 with high bone quality. In some embodiments, one or more bridging links are connected between the plate and a terminal link at one end of the structure along the rib. Although the bone quality of two ribs is discussed and depicted in FIG. 2B, this is merely for illustrative purposes and the embodiments of the present invention can measure the bone quality of each rib or more than two ribs connected to the sternum 205.

In step 404, a structure is assembled using the modular system 100 based on the characteristics of the anatomy determined in step 402. In an embodiment, in step 404 a plate 110' is selected among the plurality of plates (110, 110', 110", 110''', 110'''', 110''''') based on one of the dimensions of the sternum 205 measured in step 402, e.g. the length 232. In an example embodiment, the plate 110' is selected based on a length of the plate being the most proximate to the length 232 from among the plurality of plates (110, 110', 110", 110''', 110'''', 110''''') of the modular system 100. In another embodiment, in step 404, a link 132' is selected and the male connector of the snap connector 106, 106' of the link 132' is rotatably received in the ring connector 104, 104' in a lower left corner of the plate 110'. In this embodiment, the link 132' is then rotated relative to the plate 110' until the link 132' is approximately oriented at a same angle as the angle 227 that the rib 212a is oriented at a connection joint with the sternum 205. In another example embodiment, a second link 132' is similarly rotatably received in the ring connector 104, 104' in a lower right corner of the plate 110' and rotated related to the plate 110' until the link 132' is approximately oriented at a same angle as the angle 227 that the rib 214a is oriented at the connection joint with the sternum 205. In yet another embodiment, a pair of links 132 are selected and the male connectors of the snap connector 106, 106' of each link 132 are rotatably received in the ring connectors 104 at the top corners of the plate 110'. In an example embodiment, the links 132 are rotated within the ring connectors 104, 104' so to be oriented along the sternum 205. In other embodiments, one or more of the plates 110'''', 110''''' are selected based on the length 232 and/or such that one or more of the distal terminals 102a, 102b, 102c, 102d are oriented along the angle 227 of the rib 212a and reach the outer region 222, 226 of the ribs 212 with high bone quality. Thus, the plates 110'''', 110''''' can be employed which advantageously do not require a link be connected to the plate in order to connect the modular system along the outer region 222, 226 of the rib 212a.

In step 404, in an embodiment a link is selected among the links based on the width 234 measured across the sternum 205 between the ribs 212b, 214b. In an embodiment, the link 124 is selected among the links since the length of the link 124 is most proximate to the measured width 234 from among the links of the system 100. In an embodiment, in step 404 the link 124 is also selected since the link 124 features ring connectors 104, 104' at the opposite ends of the link and one desired characteristic of the assembled structure 200 is to connect second links (e.g. one second link or one or more bridging links connected to a terminal link) to each end of the link 120 to bridge over an inner region 220, 224 of the ribs 212 with low bone quality in order to reach an outer region 222, 226 of the ribs 212 with high bone quality. Thus, in an embodiment in step 404 two links 132 are also selected and the male connector at the snap connector 106, 106' of each link 132 is rotatably received in the ring connector 104, 104' at the ends of the link 124. The links 132 are then rotated within each ring connector 104, 104' until the links 132 are aligned along the ribs (e.g. based on the angle 227 of the rib 212) and bridge over the inner region 220, 224 so that the terminal 102 of the links 132 reaches the outer region 222, 226. This advantageously ensures that the threaded fastener can be secured into the bone with the high quality. In other embodiments, one or more bridging links can be positioned between the link 124 and the link 132 (e.g. terminal link) so to provide flexibility to the user in forming the structure 200.

In step 406, the assembled structure in step 404 is then aligned with the anatomy of the subject including the bone with the fracture. In an embodiment, step 404 is performed at a table that is separate from the subject and thus the medical practitioner may use visual memory and/or physical measurements of the subject anatomy to assemble the structure. In this example embodiment, in step 406 the medical practitioner picks up the assembled structure and brings it over to the subject and aligns the assembled structure with the anatomy of the patient with the bone and the fracture, e.g. aligns the assembled structure with the ribs and sternum. In an example embodiment, in order to ensure that the plates and/or links of the assembled structure do not disassemble, the male connector and female connectors feature the tabs 164 that engage the inner diameter of the ring connector 104 to prevent the links and plates of the assembly from coming apart. In some embodiments, in step 404 one or more fasteners can be secured through one or more terminals 102, ring connectors 104 and/or snap connectors 106, e.g. to maintain angular orientations of the link 132' along the ribs 212a, 214a during step 406. This makes it easier for the medical practitioner to align the assembled structure with the sternum 205 and ribs 212 in step 406.

In step 408, it is determined whether the assembled structure in step 406 lines up with the subject anatomy including the bone having the fragment. In an embodiment, the determination in step 408 is visually performed by a medical practitioner (e.g. surgeon). In an embodiment, in step 408 it is determined that the assembled structure lines up with the subject anatomy if the plates are aligned with the dimensions of the bones, the links are aligned with the angles of any adjacent bones and/or additional links properly bridge over bone regions with low bone quality to bone regions of high bone quality. In an example embodiment, in step 408 it is determined that the assembled structure 200 lines up with the sternum 205 and ribs 212 if the plate 110' length properly extends the length 232, e.g. from the initial location to the juncture of ribs 212a, 214a; that the links 132 connected to the top corners of the plate 110' are oriented along the sternum 205 and the terminal 102 of the link 132 is over high quality areas on the sternum 205; the links 132' connected to the bottom ring connectors 104 of the plate 110' are properly aligned with the ribs 212a, 214a and extend over high quality areas of the ribs; that the link 124 has a length that is about equal to the width 234 and the links 132 extend along the ribs 212b, 214b and bridge over the region 220, 224 of low bone quality to the region 222, 226 of high bone quality. If any of these criteria are not met, it is determined that the assembled structure does not line up and the method proceeds to block 410. If these criteria are met, it is determined that the assembled structure does line up and the method proceeds to block 412.

In step 410, the assembled structure of step 406 is adjusted based on the misalignment determined in step 408. In an example embodiment, if it is determined that the plate 110' extends too far along the sternum 205 (e.g. the length of the plate 110' exceeds the length 232), in step 410 the plate 110 is selected which has a slightly smaller length than the plate 110'. In another example embodiment, if it is determined that the terminals 102 of the links 132 attached to the top corner ring connectors 104 of the plate 110' are over a region of low bone quality, links with longer length are selected in step 410 in order to extend beyond the region of low bone quality to a region of high bone quality so that the fasteners can be advantageously secured into a region of high bone quality. In other embodiments, one or more bridging links are connected between the plate and the terminal link, so to ensure that the terminal 102 of the terminal link reaches the region of high bone quality and the one or more bridging links extend over the region of low bone quality. In yet another embodiment, in step 410 if the angular orientation of the links 132' connected to the lower corner ring connector 104 of the plate 110' are not aligned with the ribs 212a, 214a, in step 410 the angular orientation of the links 132' is adjusted based on the angles 227 so that the links 132' are oriented with the ribs 212a, 214a. In yet another embodiment, in step 410 if the links 132 attached to the ring connectors 104 on the opposite ends of the link 124 do not extend to the region 222, 226 of high bone quality, the links 132 are replaced with links having a longer length.

In an embodiment, steps 406, 408, 410 are repeated until the assembled structure is aligned with the anatomy of the subject including the bone with the fragment.

In step 412, the assembled structure 200 is secured to the anatomy of the patient, e.g. to the bone with the fragment such as to opposite sides of the bone fragment. In an embodiment, where the bone is the sternum 205, in step 412 the assembled structure 200 is secured to opposite sides of the fragment 210. In an example embodiment, fasteners (e.g. externally threaded fasteners 117, 119) are secured through the internally threaded hole 172 of each engaged male and female connector, e.g. through each snap connector 106 received within the ring connector 104. In another embodiment, fasteners are optionally secured through one or more terminals 102 of the plates and/or links, depending on whether the medical practitioner believes that additional fasteners are necessary to secure the structure 200 to the bone. In yet another example embodiment, fasteners are also secured through the snap connectors 106 and/or terminals 102 of the connectors in the links that were not matingly engaged to the female connector, e.g. the inner diameter of a snap connector 106, also depending on whether or not the medical practitioner believes these additional fasteners are necessary to adequately secure the structure 200 to the bone. In some embodiments, the anatomy of the subject is used to determine whether to secure fasteners into the terminals 102 and/or snap connectors 106. In an example embodiment, such as where the terminals 102 and/or snap connectors 106 extend over a region with low bone quality, fasteners are not secured through the terminals 102 and/or snap connectors 106, so to avoid damaging the low quality region.

In step 412, in one embodiment, one or more wires or bands are secured around the structure 200 secured to the anatomy of the patient. In one embodiment, the one or more wires or bands are secured around the bone fragment and into one or more grooves of the links and/or the plates of the structure 200. In this embodiment, the wires or bands are wrapped around the links and/or plates in a direction that is about orthogonal to the links and/or plates so that a width of the wires or bands is positioned in the groove of the links and/or plates. In yet another embodiment, no wires or bands are employed and the structure 200 is secured to the bone using the fasteners through the opening of the structure 200 previously discussed.

Figure 5A:
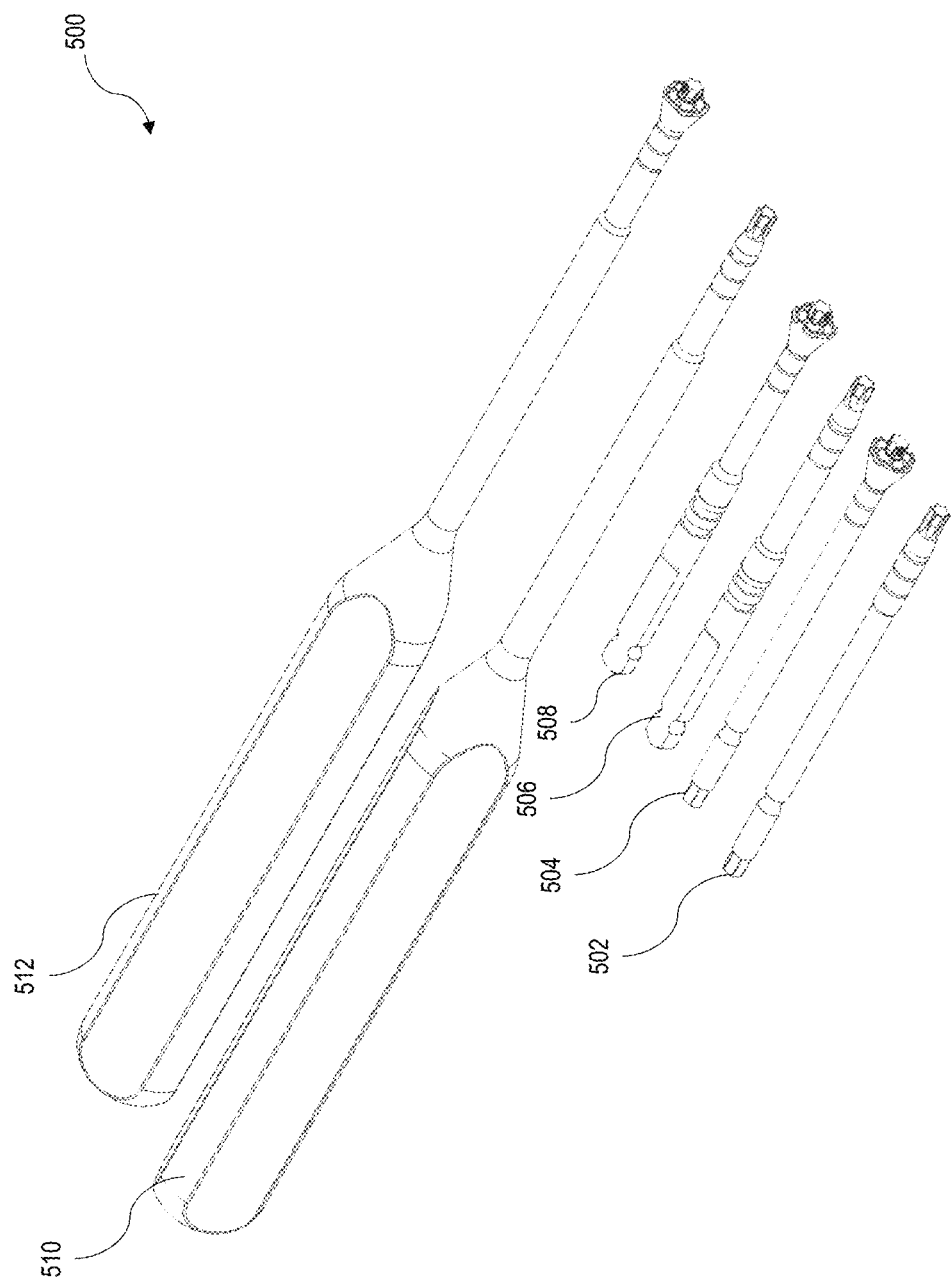
FIG. 5A is an image that illustrates an example of a tool assembly for use in performing one of more steps of the method of FIG. 4, according to an embodiment.

In an embodiment, in step 404 a tool is utilized to assemble the structure using the modular system and/or in step 412 the tool is also utilized to secure the assembled structure 200 to the anatomy of the patient. FIG. 5A is an image that illustrates an example of a tool assembly 500 for use in performing one of more steps of the method 400 of FIG. 4, according to an embodiment. In an embodiment, the tools of the tool assembly 500 are configured to be inserted within the head of a particular fastener 117, 119 (e.g. T10 screw), however the tool assembly 500 can be configured to be inserted within the head of any fastener known in the art. In an embodiment, each tool of the tool assembly 500 can be used to perform step 404 and/or step 412. In one embodiment, the tools 504, 508, 512 can perform steps 404 and step 412, whereas the tools 502, 506, 510 can perform step 412 but not step 404. In an example embodiments, the tools 502, 504 are employed with a power driver. In another example embodiment, the tools 506, 508 are employed with a ratcheting screwdriver (e.g. AO connection). In still another example embodiment, the tools 510, 512 are screwdrivers with conventional handles.

Figure 5B:
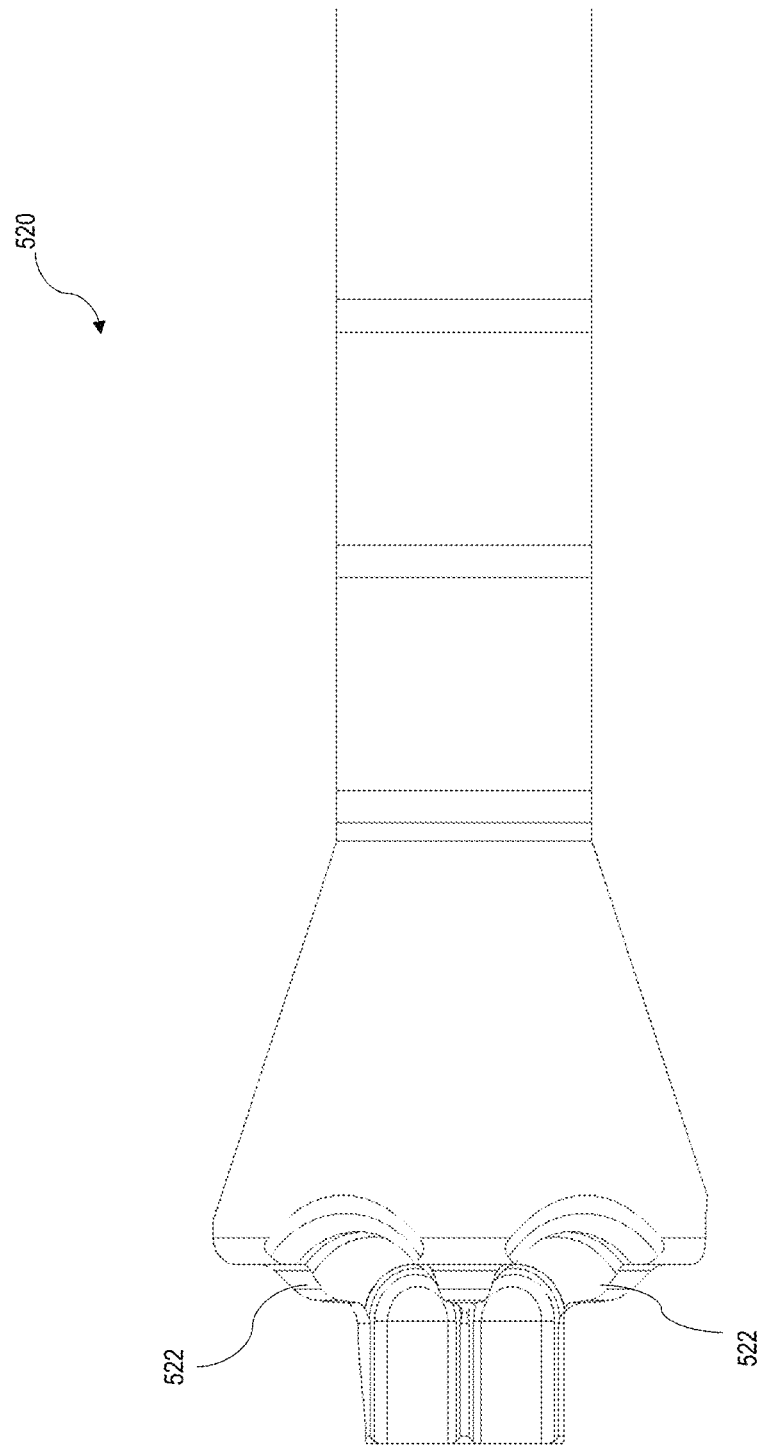
FIGS. 5B through 5D are images that illustrate an example of one tool of the tool assembly of FIG. 5A, according to an embodiment.
Figure 5C:
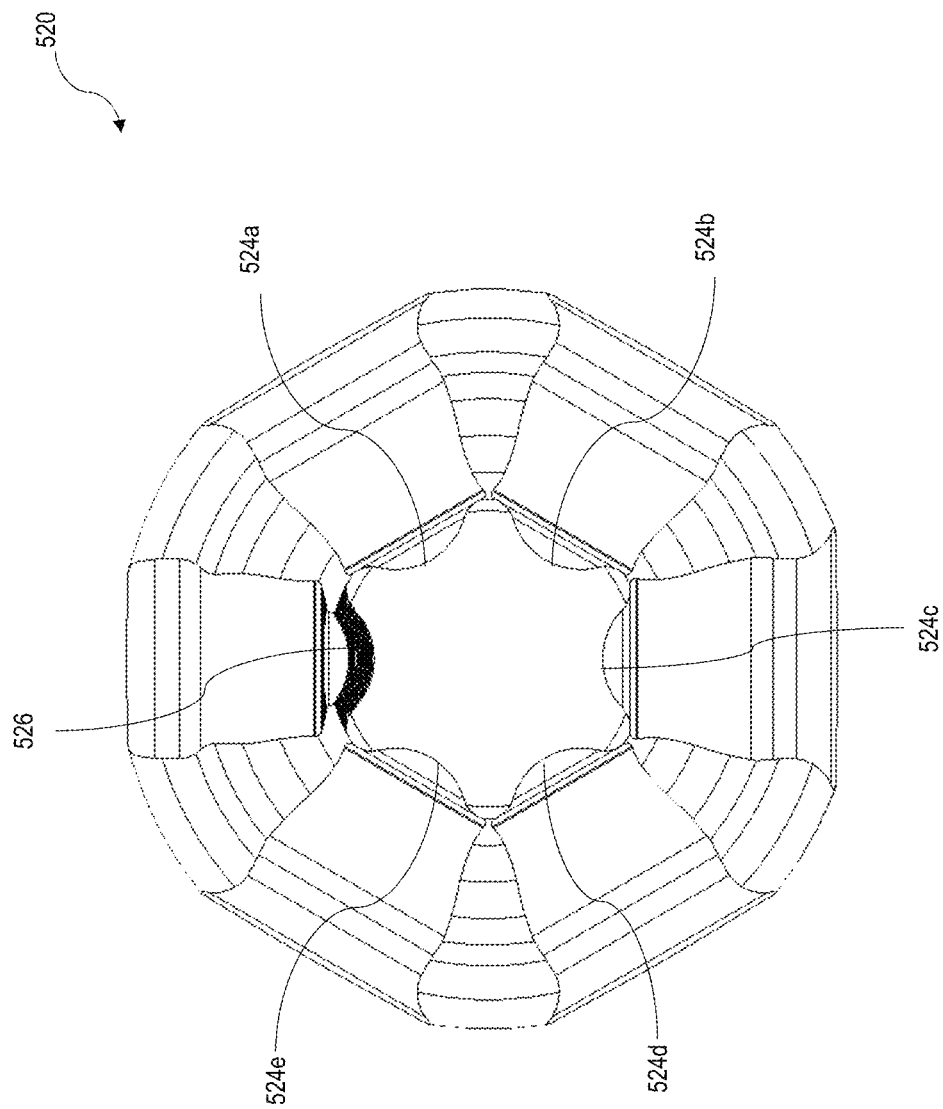
Figure 5D:
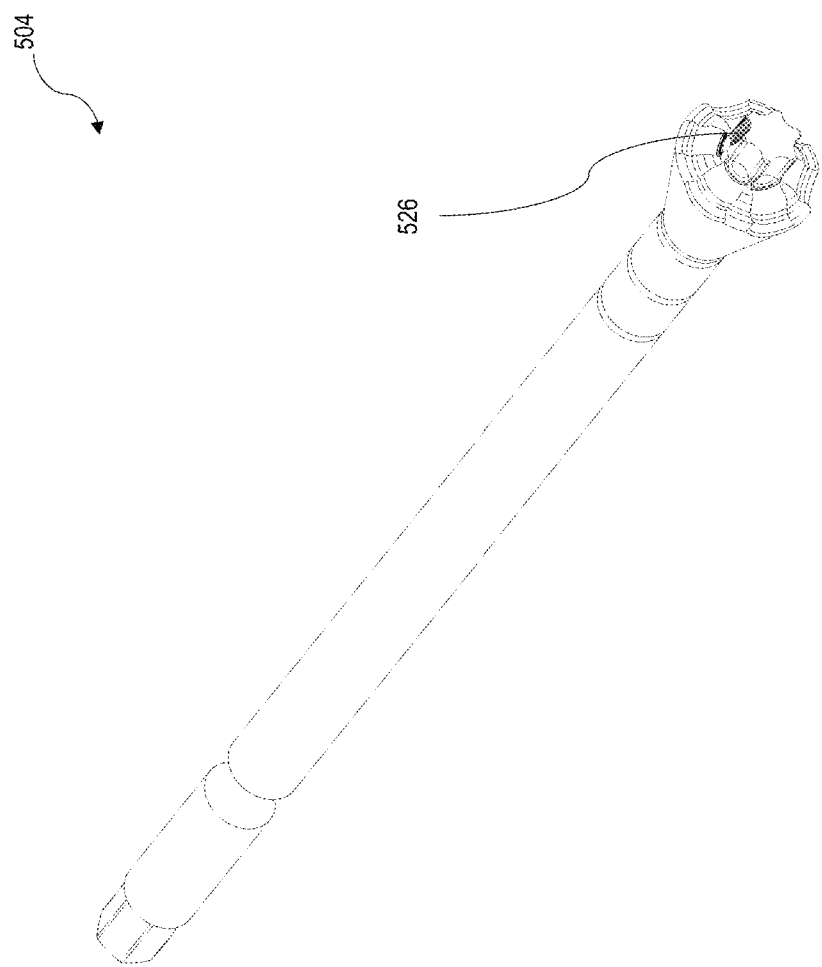
Figure 5E:
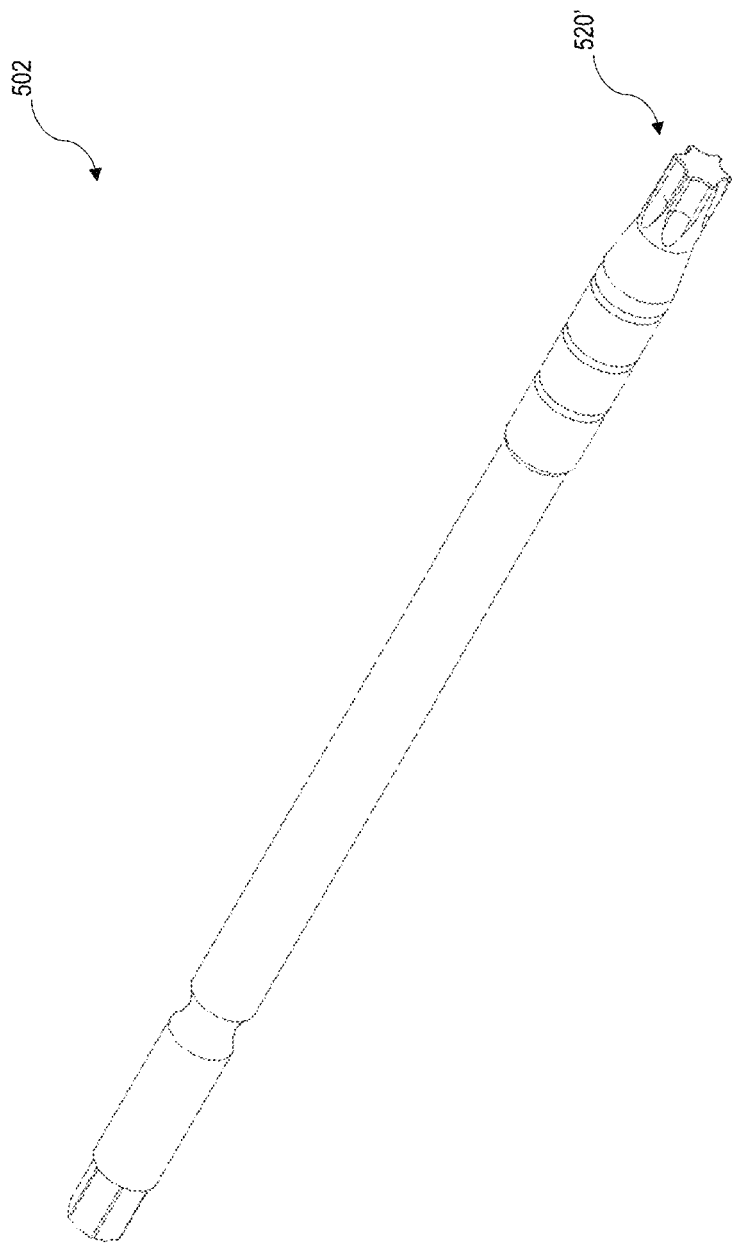
FIG. 5E is an image that illustrates an example of one tool of the tool assembly of FIG. 5A, according to an embodiment.
Figure 5F:
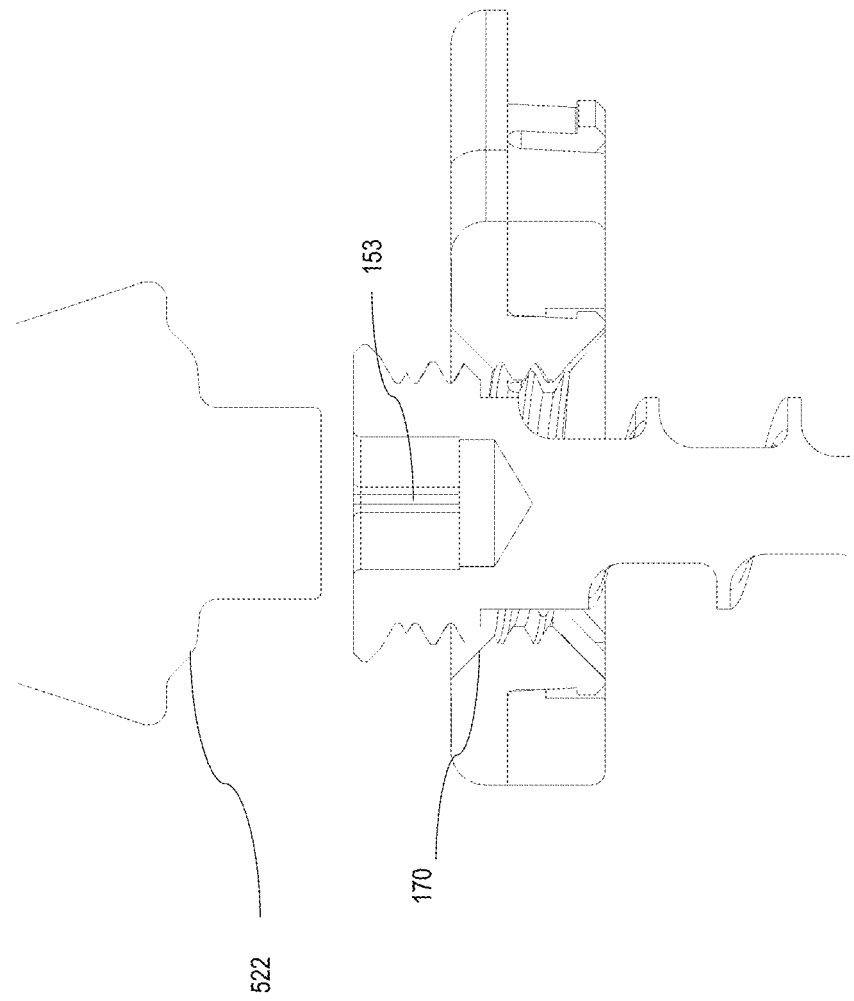
Figure 5G:
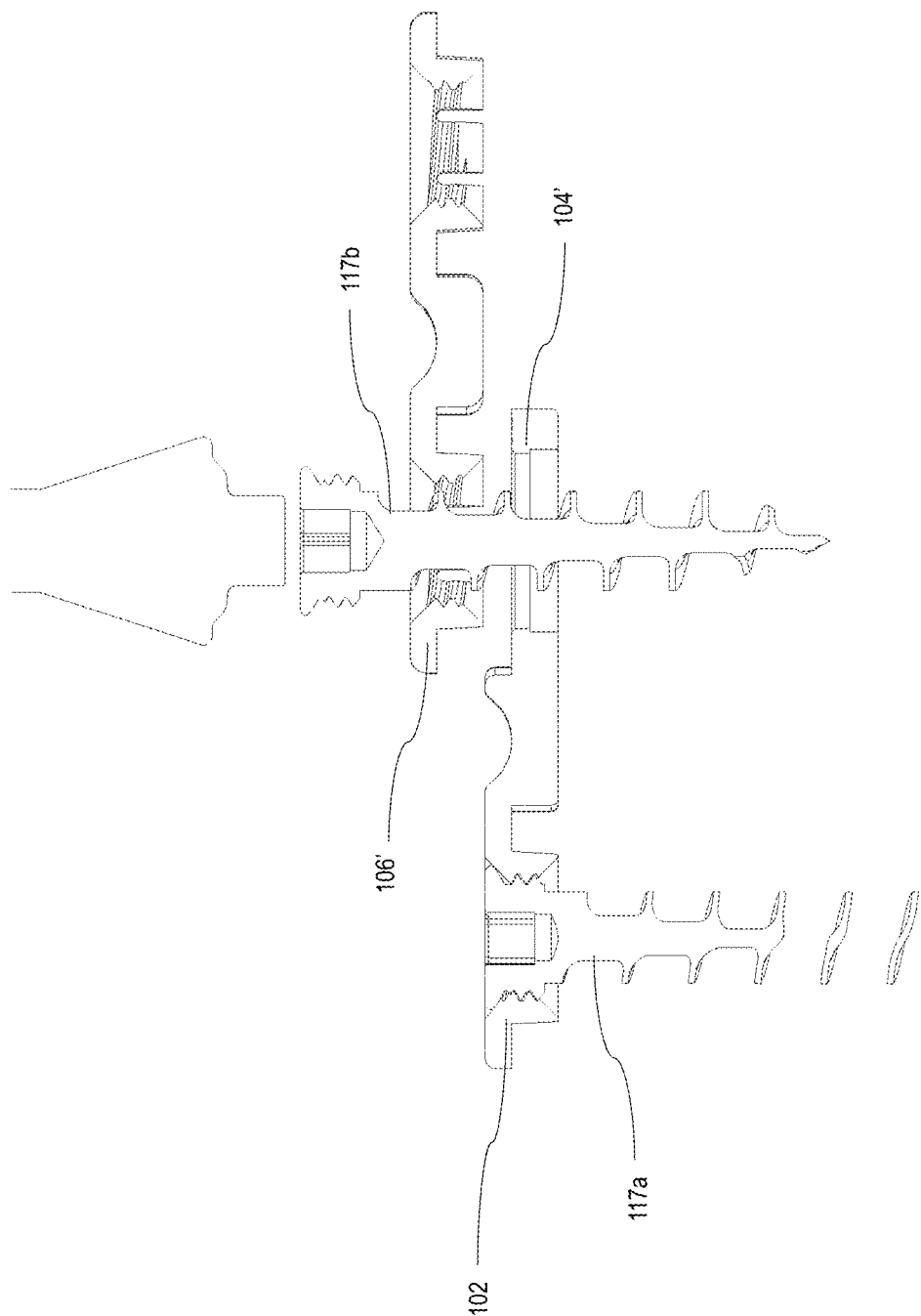
Figure 5H:
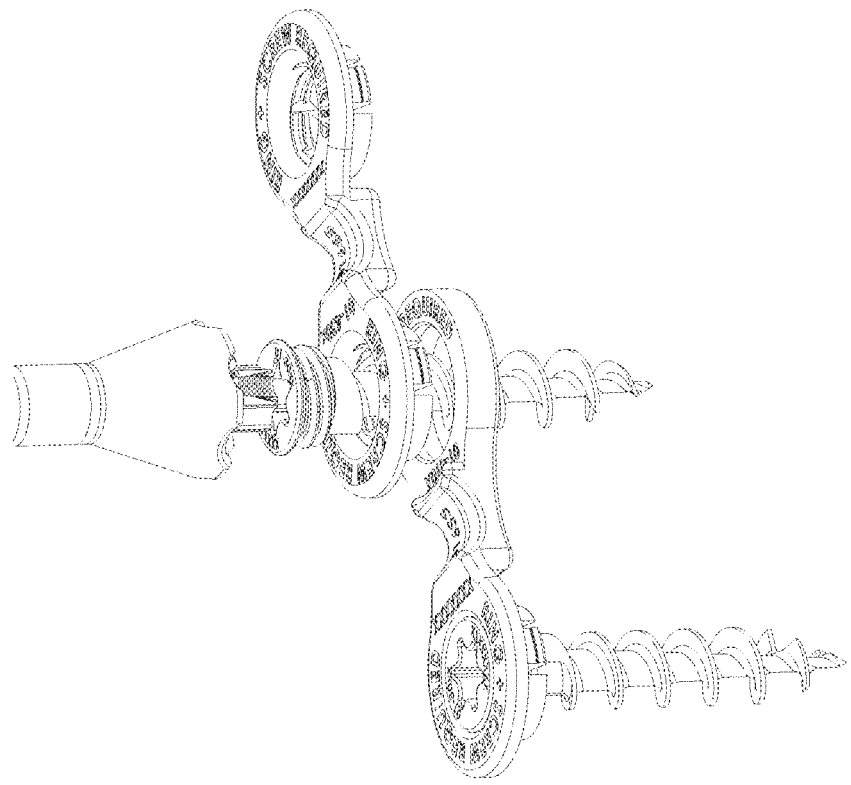
Figure 51:
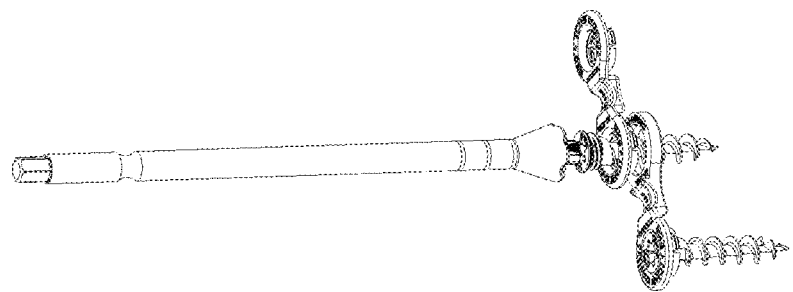
Figure 5J:
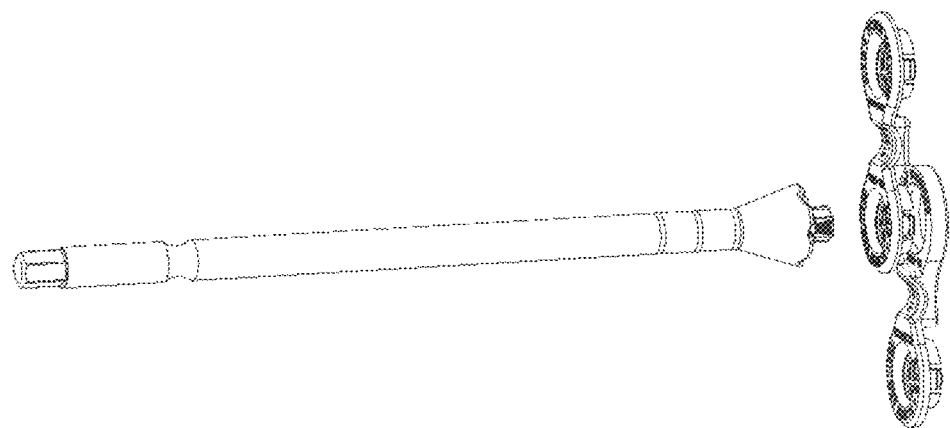
Figure 5K:
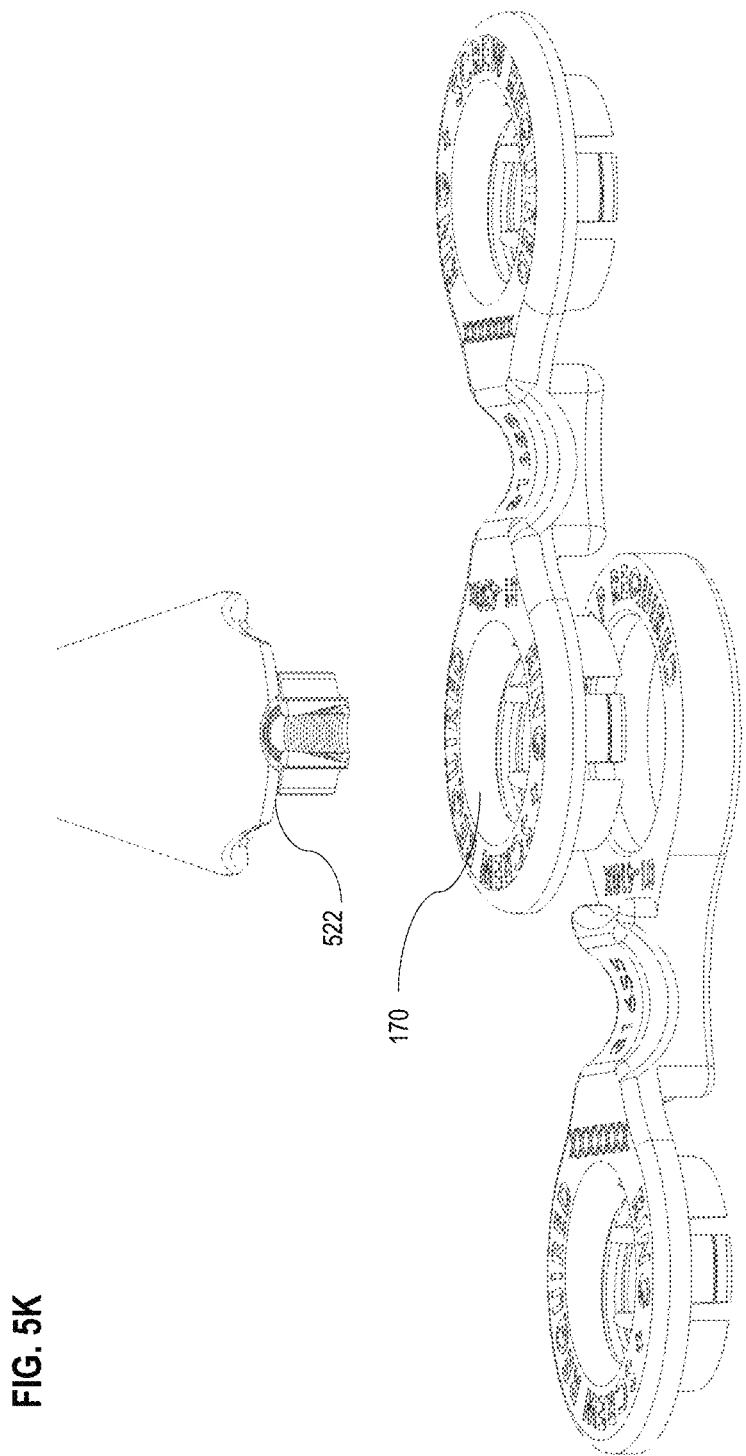
Figure 5L:
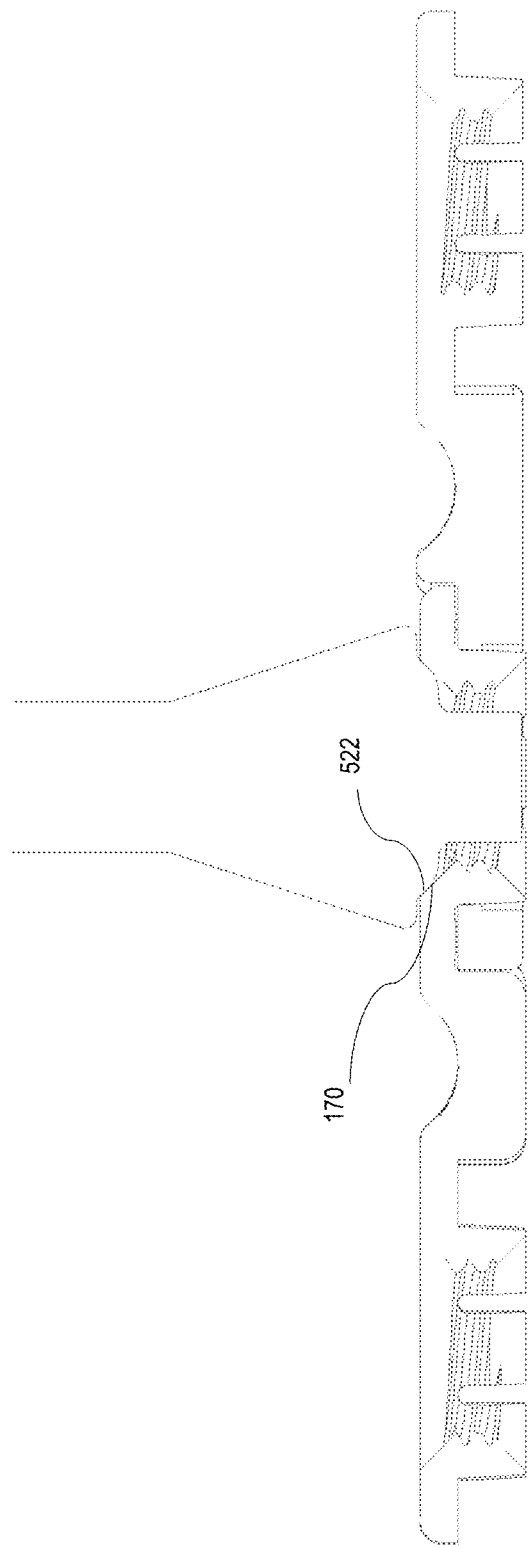

FIGS. 5B through 5D are images that illustrate an example of one tool 504, 508, 512 of the tool assembly 500 of FIG. 5A, according to an embodiment. In an embodiment, a tip 520 of the tool 504, 508, 512 features an arcuate or chamfered surface 522 around a perimeter of the tip 520 and a plurality of lobes 524a through 524e and 526, as discussed below. FIG. 5E is an image that illustrates an example of the tool 502 of the tool assembly 500 of FIG. 5A, according to an embodiment that features a tip 520' that is different from the tip 520 of the tool 504 of FIG. 5B since it excludes the chamfered surface 522. The tools 506 and 510 have a similar tip 520' as shown in FIG. 5E.

FIGS. 5F through 5L are images that illustrate an example of the tool 504 of FIGS. 5B through 5D being used to perform one or more steps of the method of FIG. 4, according to an embodiment. The tools 508, 512 can also be used in a similar manner as the tool 504 in FIGS. 5F through 5L. In an embodiment, during step 404 the arcuate (or chamfered surface) 522 of the tool 504 is used to engage the conical surface 170 (FIGS. 5J through 5L) of the snap fastener 106, 106' to apply force evenly around the circumference of the conical surface 170. In one embodiment, the curvature of the arcuate surface 522 is based on the curvature of the conical surface 170 (e.g. is shaped so to engage the conical surface 170 uniformly around the circumference of the snap fastener 106, 106'). In an embodiment, the arcuate or chamfered surface 522 extends around the circumference of the tool tip 520 and thus an even force is applied around the circumference of the conical surface 170. The inventors recognized that the tool 504, 508, 512 advantageously minimizes the risk that can occur when the snap fastener 106, 106' is manually pressed by the user into the ring connector 104, 104' (e.g. uneven force around the circumference of the connectors 104, 106, which may cause one or more tabs 164, 164' to break or crack.

In another embodiment, as shown in FIGS. 5F through 5I, the tool 504 can also be used to perform step 412 (e.g. secure the fastener 117, 119 through the threaded opening 172 in the snap fastener 106, 106' and/or through the threaded opening 172 of the terminal 102 and into the bone of the patient). Additionally, any of the other tools 506, 508, 510, 512 can be used to perform step 412 in the manner shown in FIGS. 5F through 5I. In an embodiment, the tip 520 of the tool 504 (and the tip 520' of the tool 502) features a tapered lobe 526 (FIG. 5C) where the remaining lobes 524a through 524e are non-tapered. In an embodiment, the tapered lobe 526 is tapered in a direction of a longitudinal axis of the tool 504, such that the tapered lobe 526 is conical in shape (e.g. arc length varies with distance from the tip 520) along the longitudinal axis whereas the remaining lobes 524a through 524e are cylindrical in shape (e.g. arc length does not vary with distance from the tip 520). In yet another embodiment, in addition to being tapered along the direction of the longitudinal axis, the tapered lobe 526 is tapered in a radial direction (e.g. the plane of FIG. 5C) so that the tapered lobe 526 is tilted and forms an angle relative to the longitudinal axis of the tool 502. In an example embodiment, as shown in FIG. 5C, the tapered lobe 526 is tapered in the radial direction at an orientation away from the longitudinal axis. The inventors of the present invention recognized that the tapered lobe 526 advantageously permitted the tool 504 to engage the female opening 153 (FIG. 5F) and hold the fastener 117, 119 securely on the tip 520 of the tool 504 so that it does not fall from the tip 520 as the user it aligning the fastener 117, 119 with the threaded opening 172 of the snap fasteners 106, 106' (see FIGS. 5F through SI). This is particularly advantageous in the realm of surgical procedures encompassed by the method 400, where it is imperative that the fastener 117, 119 does not fall from the tool 504 and into the body of the patient.

U.S. patent application Ser. No. 15/864,489 filed on Jan. 8, 2018 and assigned to the assignee of the present invention is incorporated by reference herein. In another embodiment, prior to step 412, a fusion strip is positioned between the opposite sides of the fracture in the bone. In an example embodiment, prior to step 412, the fusion strip is positioned between opposite sides of the fracture 210 in the sternum 205, as disclosed in the '489 application. In yet another embodiment, prior to step 412, the method includes placing a fusion strip including osteoconductive material on an undersurface of the plate of the assembled structure, as disclosed in the '489 application.

Figure 2C:
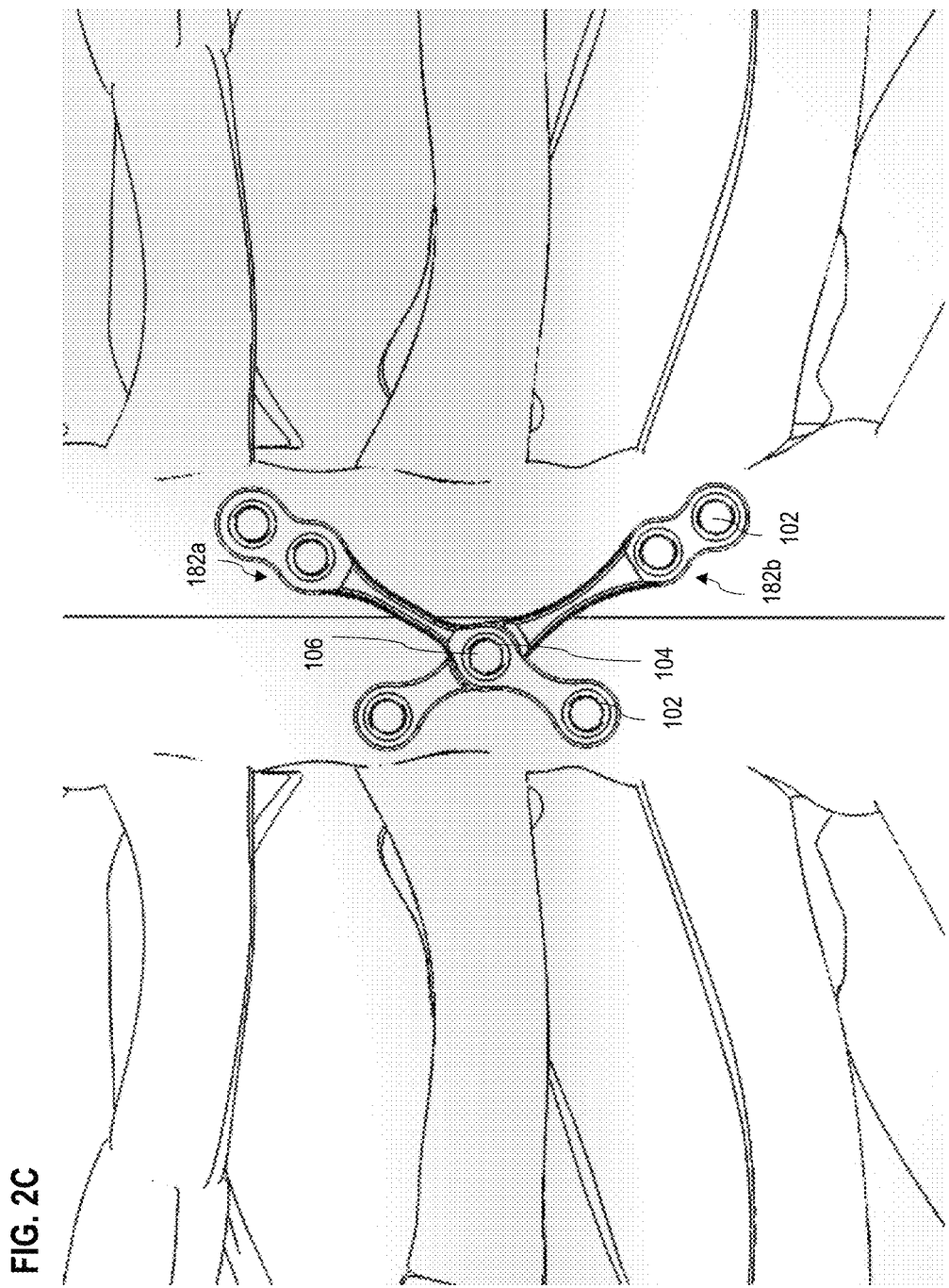
FIG. 2C is an image that illustrates a front view of a structure assembled with the modular system of FIGS. 2A-2B and aligned with a fracture in a sternum of a subject, according to an embodiment.
Figure 2D:
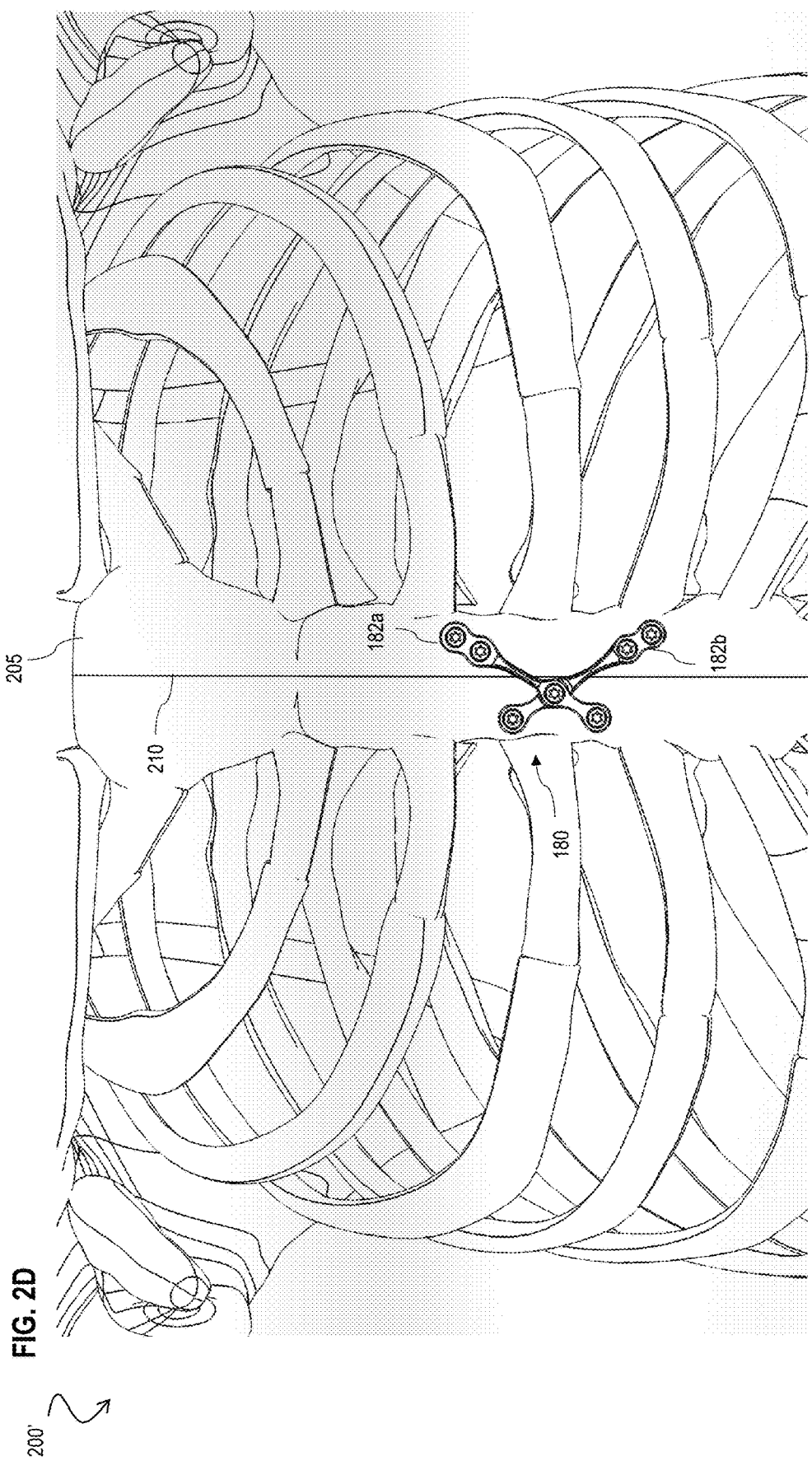
FIG. 2D is an image that illustrates an example of a front view of the structure of FIG. 2C secured to the sternum, according to an embodiment.

FIGS. 2C-2D are images that illustrate a front view of a structure 200' assembled with the modular system of FIGS. 2A-2B and aligned with a fracture in a sternum 205 of a subject, according to an embodiment. In an embodiment, assembled structure 200' includes a first link 182a with a snap connector 106 and terminals 102 and a second link 182b with a ring connector 104 and terminals 102. In an embodiment, the first link 182a excludes the snap connector 106 at a midpoint along the linear axis 121 of the first link 182a and the second link 182b excludes the ring connector 104 at a midpoint along the linear axis 121 of the second link 182b. This structural arrangement is provided so that when the snap connector 106 of the link 182a matingly engages the ring connector 104 of the link 182b, the pair of links 182a, 182b can be symmetrically positioned on either side of the fracture 210 in the sternum 205 and the rotation axis (defined by the snap connector 106 positioned within the ring connector 104) is offset from the sternum fracture 210. This is advantageous since it permits a symmetric structure to be positioned about the sternum fracture 210 with a rotation axis (e.g. defined by the snap connector 106 positioned in the ring connector 104) offset from the sternum fracture 210. In an embodiment, a male connector including the snap connector 106 of the first link 182a is rotatably received within a female connector including the ring connector 104 of the second link 182b (e.g. where the links 182a, 182b are rotatably coupled in FIG. 2D) so that the mating connection (e.g. snap connector 106 within the ring connector 104) is offset from the fracture 210 in the sternum 205. In step 412, three fasteners are secured in the link 182a, 182b including a first fastener into the snap connector 106 rotatably positioned within the ring connector 104, a second fastener in the first link 182a (e.g. bottom left terminal 102 in FIG. 2D) and a third fastener in the second link 182b (e.g. bottom right terminal 102 in FIG. 2D). After securing these fasteners, the links 182a, 182b are spread apart (e.g. left and right sides are spread apart, top and bottom ends are brought together) to bring the opposite sides of the fracture 210 together. In some embodiments, the fasteners are then secured in each terminal 102 of the links 182a, 182b. Then the fasteners are fully secured into the bone so to hold the links 182a, 182b in a fixed relationship and to keep the opposite sides of the fracture 210 together.

FIG. 3A is an image that illustrates a front view of a structure 300 assembled with the modular system 100 of FIGS. 2A-2B and aligned with a fracture in a hand bone 205' of a subject, according to an embodiment. In an embodiment, the method 400 is performed in a similar way as with the assembled structure 200 for the sternum 205. In an embodiment, the bands or wires may or may not be used to secure the structure 300 to the hand bone 205'. In another embodiment, features of the subject anatomy similar to the method above (e.g. dimensions of the bone, quality of the bone, dimensions of adjacent bones and/or angles of adjacent bone with the bone 205', etc.) are used to assemble the structure 300.

FIG. 3B is an image that illustrates a front view of a structure 300' assembled with the modular system 100 of FIGS. 2A-2B and aligned with a fracture in a foot bone 205" of a subject, according to an embodiment. In an embodiment, the method 400 is performed in a similar way as with the assembled structure 200 for the sternum 205. In an embodiment, the bands or wires may or may not be used to secure the structure 300' to the foot bone 205". In another embodiment, features of the subject anatomy similar to the method above (e.g. dimensions of the bone, quality of the bone, dimensions of adjacent bones and/or angles of adjacent bone with the bone 205", etc.) are used to assemble the structure 300'.

Figure 3C:
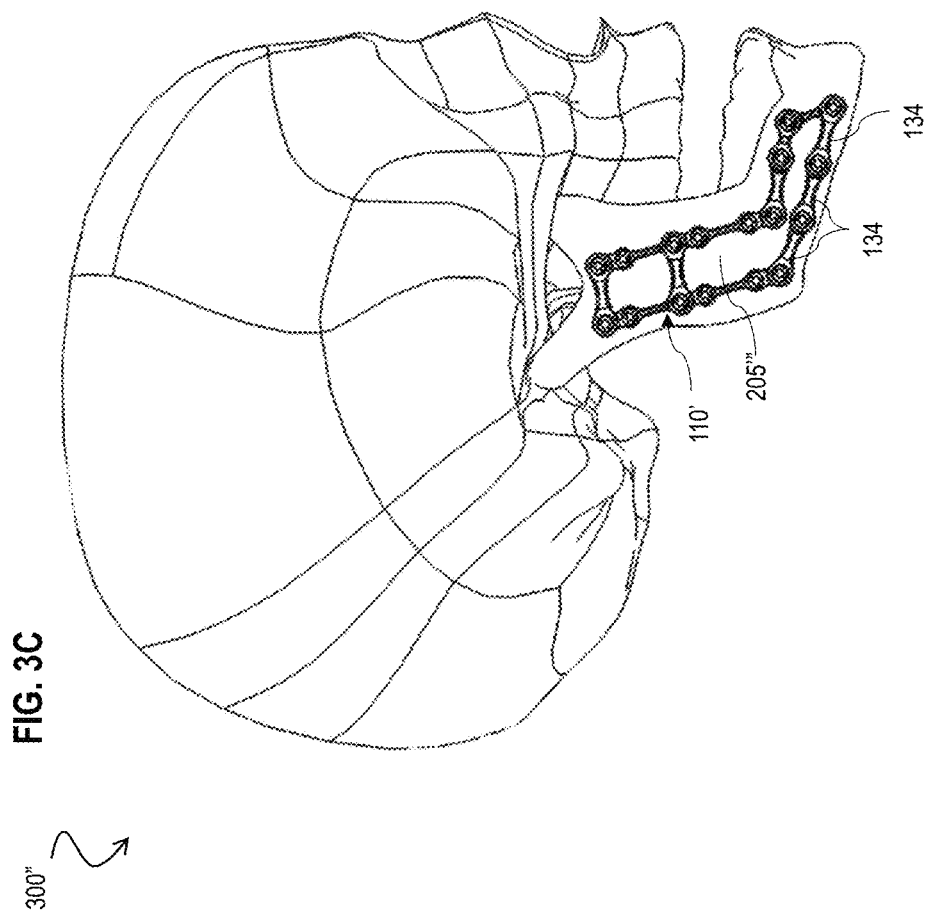
FIG. 3C is an image that illustrates a front view of a structure assembled with the modular system of FIGS. 1A-1B and aligned with a fracture in a jaw bone of a subject, according to an embodiment.

FIG. 3C is an image that illustrates a front view of a structure 300" assembled with the modular system 100 of FIGS. 2A-2B and aligned with a fracture in a jaw bone 205''' of a subject, according to an embodiment. In an embodiment, the method 400 is performed in a similar way as with the assembled structure 200 for the sternum 205. In an embodiment, the bands or wires may or may not be used to secure the structure 400 to the jaw bone 205''. In some embodiments, plates or links can be employed to form the structure 400. In another embodiment, features of the subject anatomy similar to the method above (e.g. dimensions of the bone, quality of the bone, dimensions of adjacent bones, angles of adjacent bone with the bone 205", etc.) are used to assemble the structure 400. Although FIG. 3C depicts the structure 300" assembled and aligned with a fracture in the jaw bone 205''', the structure can be assembled and aligned with a fracture on any skull bone. In yet further embodiments, a structure can be assembled to be aligned with a fracture of any bone in the subject (e.g. human subject) including small bones where the plates and/or links of the modular system can be appropriately scaled based on the size of the bone.

Although the above embodiments discuss a medical practitioner manually performing the steps of the method 400, in another embodiment, one or more steps of the method 400 can be automatically performed by a processor communicating with one or more electrical devices using a software module with one or more instructions. In an embodiment, in step 402 one or more imaging systems (e.g. X-ray, MRI, CT-scan, Ultrasound, etc.) performs a scan of the subject including a region of the subject including the bone fracture. In an embodiment, the scan of the subject provides data that indicates the one or more characteristics (e.g. dimensions, angles, bone quality, etc.). In another embodiment, in step 404 the module of the processor receives input data including the imaging data (e.g. data indicating the characteristics from step 402) from the imaging systems and data indicating each of the plates and links of the modular system 100 (e.g. which can be stored in a memory of the processor). Based on this input data, the processor determines an assembled structure of plates and/or links from the modular system 100. In one example embodiment, steps 406, 408, 410 are internally performed by the software module of the processor until the assembled structure is determined. In this embodiment, the processor either transmits a signal to display the assembled structure so that the medical practitioner can then assemble the structure by viewing the display or the processor transmits a signal to a device which automatically generates the assembled structure with the modular system 100. In this embodiment, step 412 is performed manually by the medical practitioner. In other embodiments, a device (e.g. 3D printer) could be used to generate customized links and/or plates based on the imaging data. In an example embodiment, the 3D printer could print links and/or plates that are customized to fit the dimensions and/or angles of the bones of the subject. In another example embodiment, the 3D printer could print an arcuate link that is curved with a specific radius of curvature and/or arc length so to extend from the fracture bone (e.g. sternum) to an adjacent bone (e.g. rib) and a region of the adjacent bone with high bone quality.

FIGS. 6A through 6I are images that illustrate an example of a container 600, 600', 600" for packaging one or more tools of the tool assembly 500 of FIG. 5A and/or one or more components of the modular system 100 of FIGS. 1A and 1B, according to an embodiment. In an embodiment, the container 600 (FIGS. 6A through 6C) is used to package one or more tools of the tool assembly 500 and/or one or more components of the modular system 100 (e.g. fixed plates 110"", 110"""). In yet another embodiment, the container 600' (FIGS. 6D through 6F) is used to package one or more links and/or one or more plates of the modular system 100. In yet another embodiment, the container 600" (FIGS. 6G through 6I) is used to package one or more fasteners of the modular system 100.

Figure 6A:
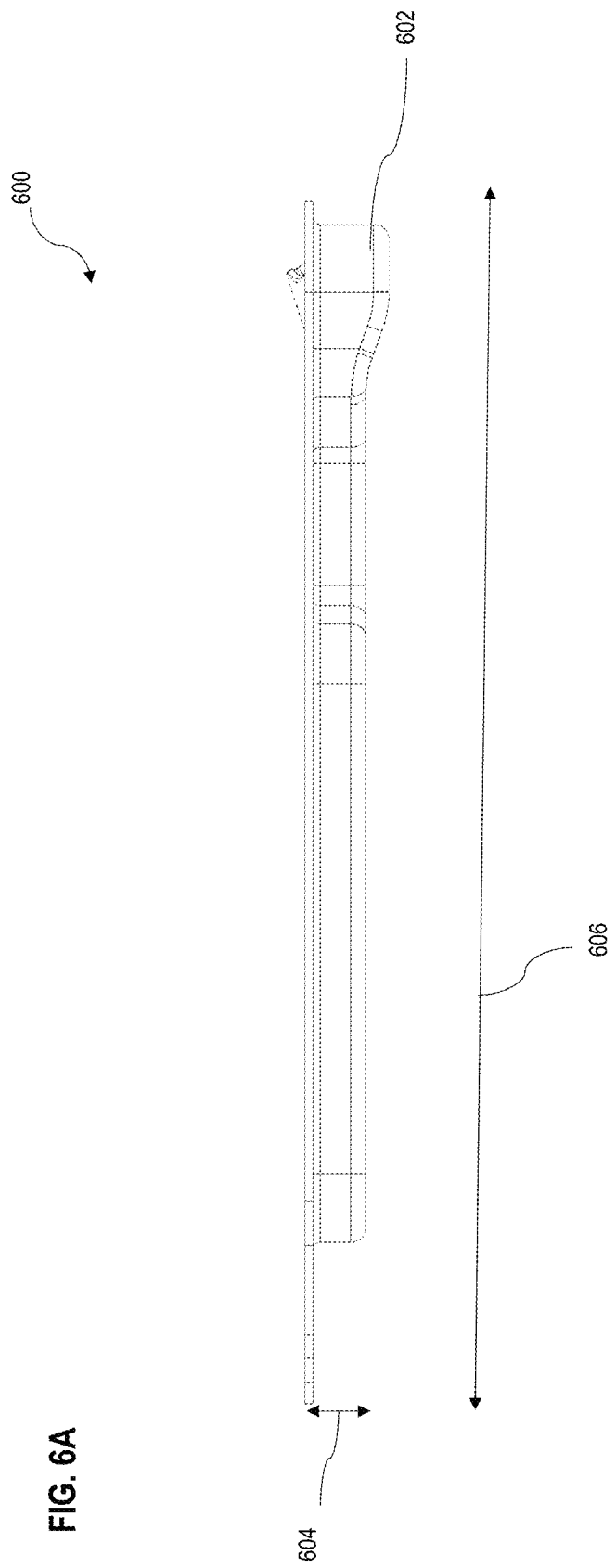
FIGS. 6A through 6I are images that illustrate an example of a container for packaging one or more tools of the tool assembly of FIG. 5A and/or one or more components of the modular system of FIGS. 1A and 1B, according to an embodiment.
Figure 6B:
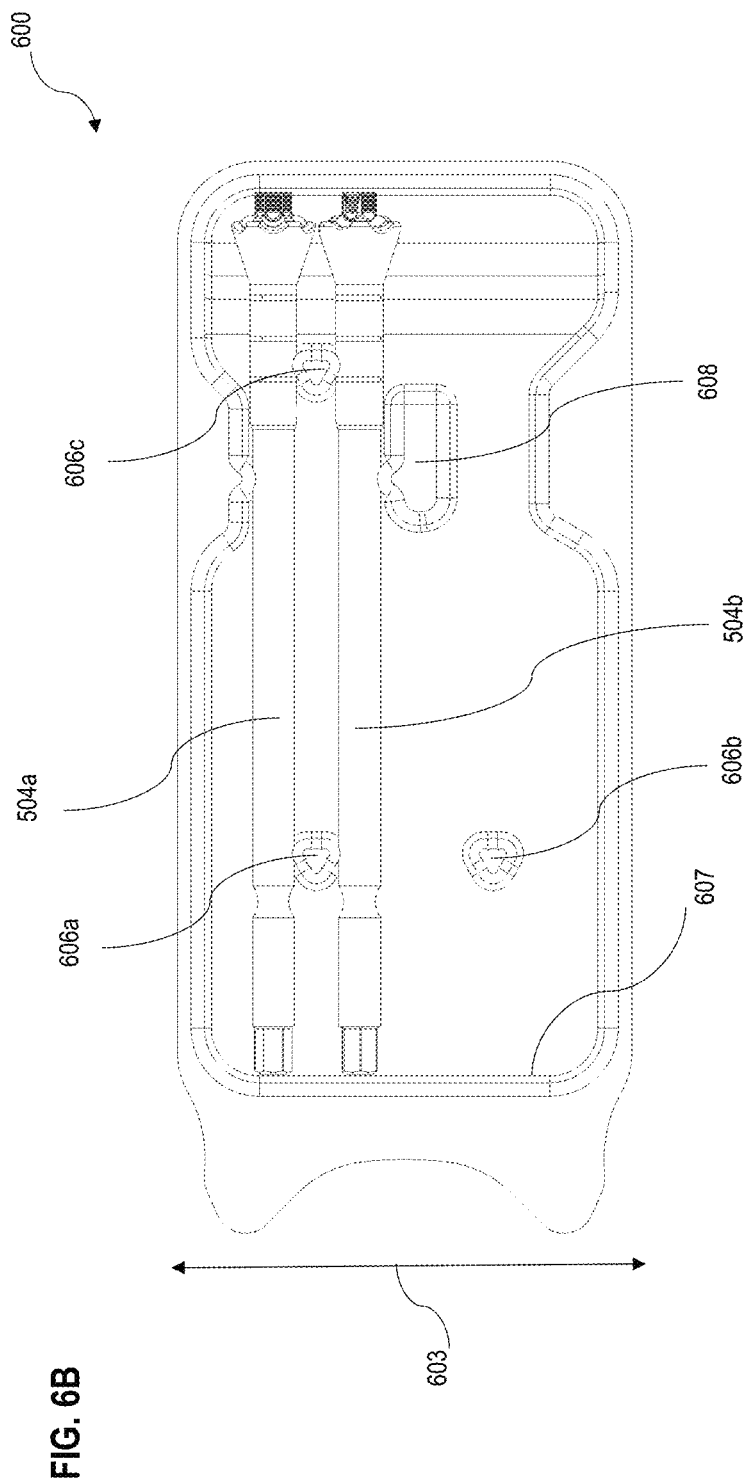
Figure 6C:
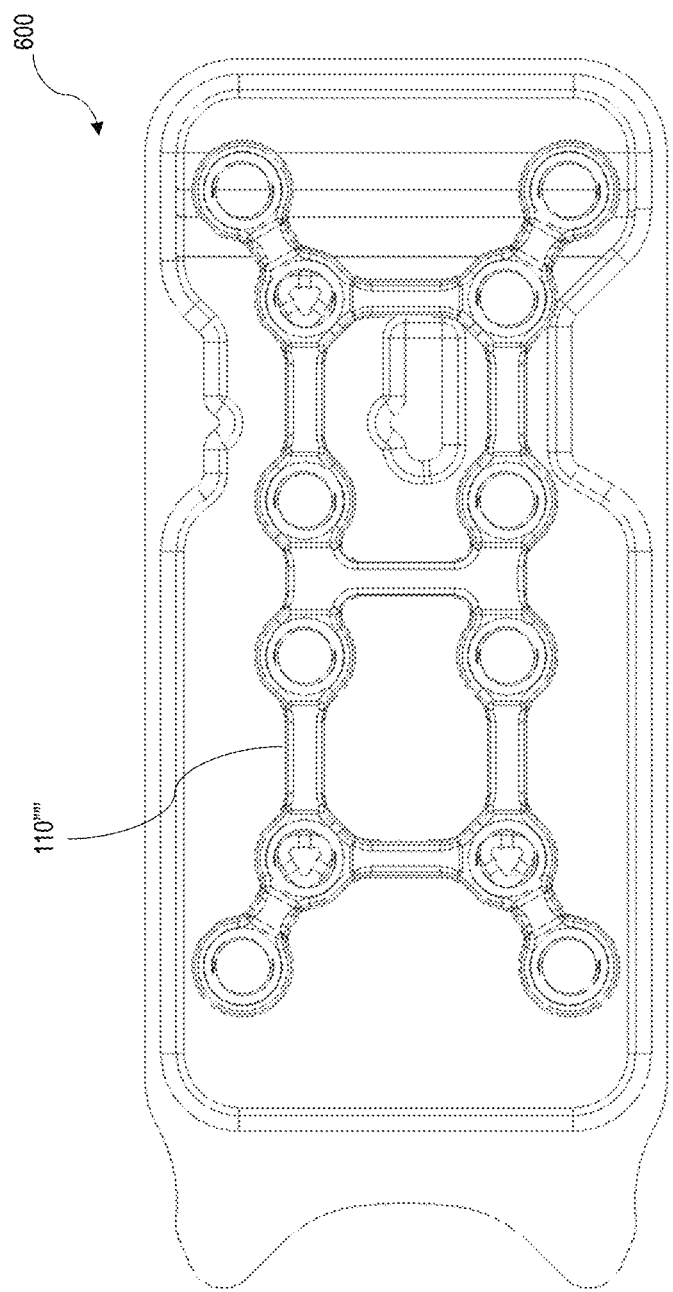
Figure 6D:
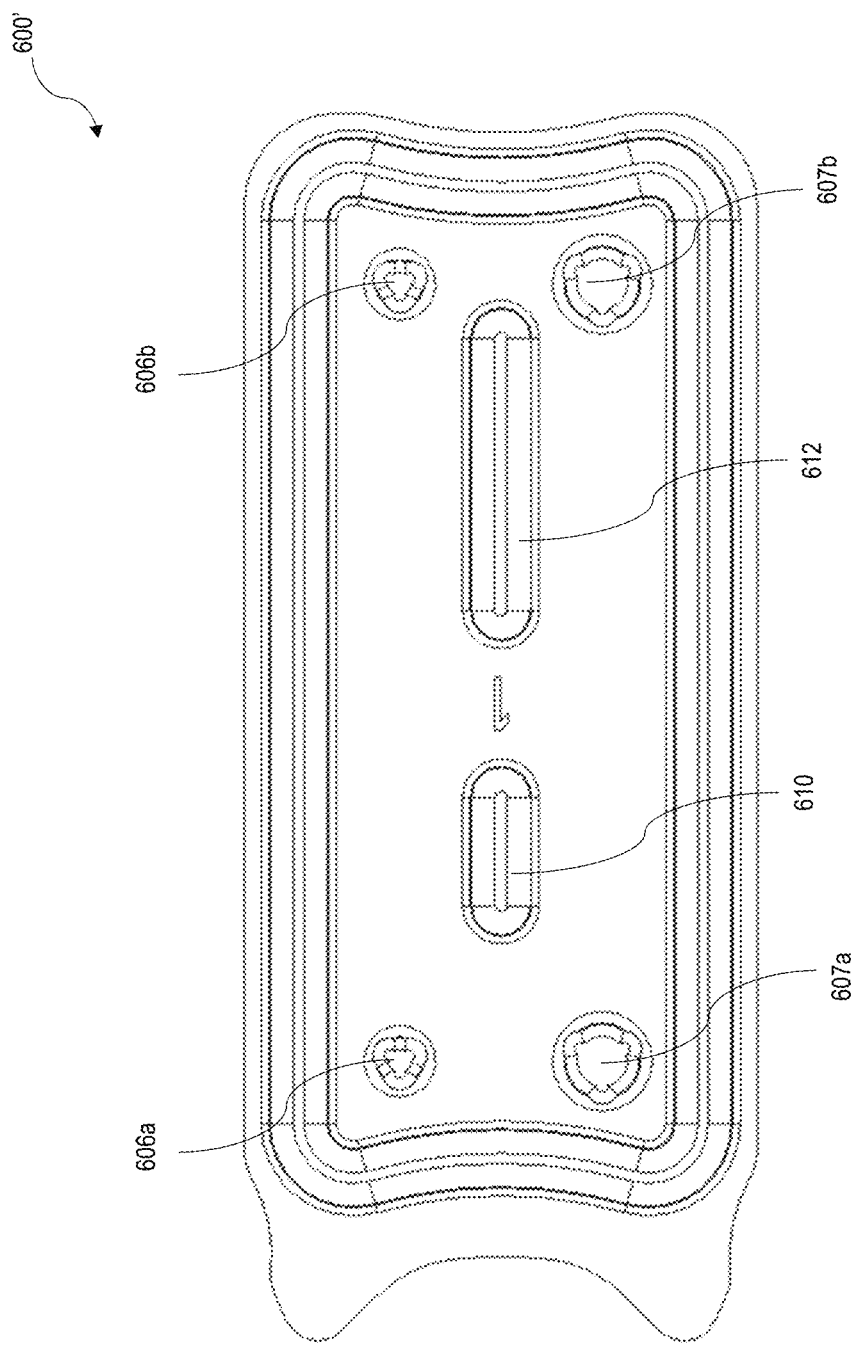
Figure 6E:
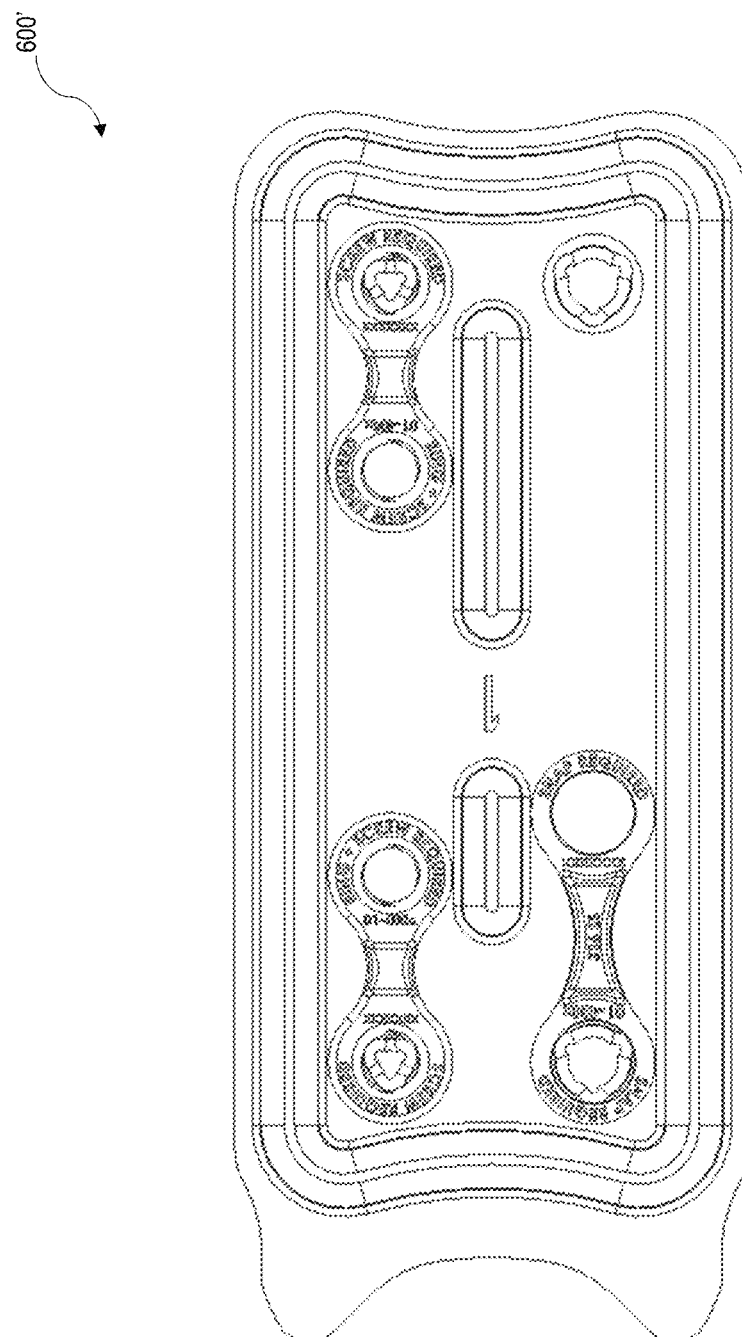

In an embodiment, the container 600, 600', 600" is made of a plastic material (e.g. Polyethylene terephthalate or PET). In an example embodiment, the container 600, 600', 600" is sterile and provides a minimum term of sterility (e.g. 5 years). In one embodiment, the container 600, 600', 600" includes a tray 602 with a height 604, a length 606 and a width 603 that are respectively sized to hold the contents discussed herein. As shown in FIG. 6B, an interior cavity of the tray 602 is defined by an inner surface 607 that extends around a perimeter of the interior cavity. In one embodiment, as shown in FIG. 6B the tray 602 includes one or more posts 606a, 606b, 606c and further includes a post 608 (e.g. larger than the posts 606) which frictionally engage one or more tools 504a, 504b from the tool assembly 500. In an example embodiment, the posts 606, 608 are thermoformed during the manufacture of the container 600. This frictional engagement advantageously holds the tools in place so that they cannot fall out of the container 600 (e.g. until they are removed manually). In one embodiment, the posts 606a, 606c and post 608 frictionally engage the tools 504a, 504b In another embodiment, FIG. 6C depicts a component of the modular system 100 (e.g. plate 100"'") secured within the tray 602 in a similar manner as the tools in FIG. 6B (e.g. frictional engagement between the posts 606, 608 and the component of the modular system 100). In an example embodiment, the posts 606 are sized to frictionally engage a terminal 102. In another embodiment, the inner surface 607 of the tray 602 frictionally engages a perimeter of the tools and/or modular system component, along with the posts 606, 608. Although FIG. 6B depicts the tray 602 holding a tool from the tool assembly 500 and FIG. 6C depicts the tray 602 holding a component of the modular system 100, in other embodiments, the tray 602 can be configured to hold a tool from the tool assembly 500 and a component of the modular system 100. However, the container 600 is not limited to any particular manufacturer make/model. In some embodiments, the component of the modular system 100 is used for cardio-thoracic procedures. Thus, in an example embodiment, the container 600 is configured to hold one or more components of a modular system 100 to be used in cardio thoracic procedures.

Figure 6F:
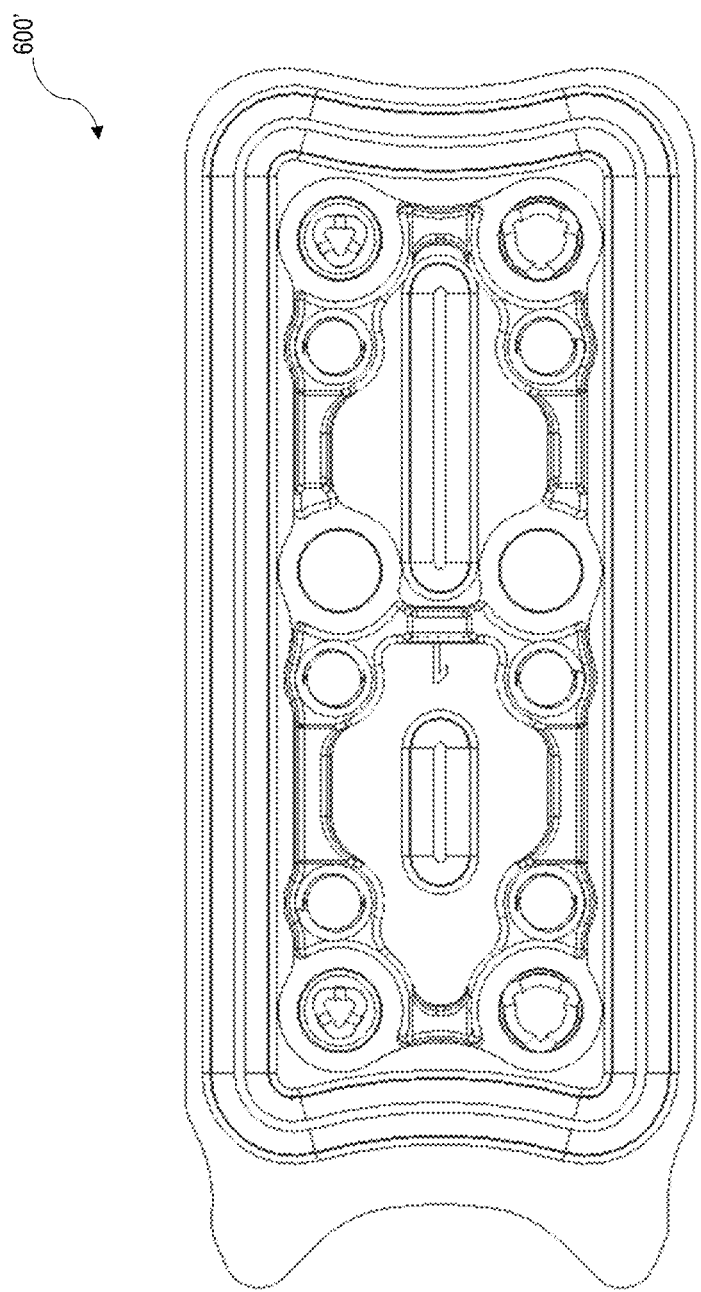
Figure 6G:
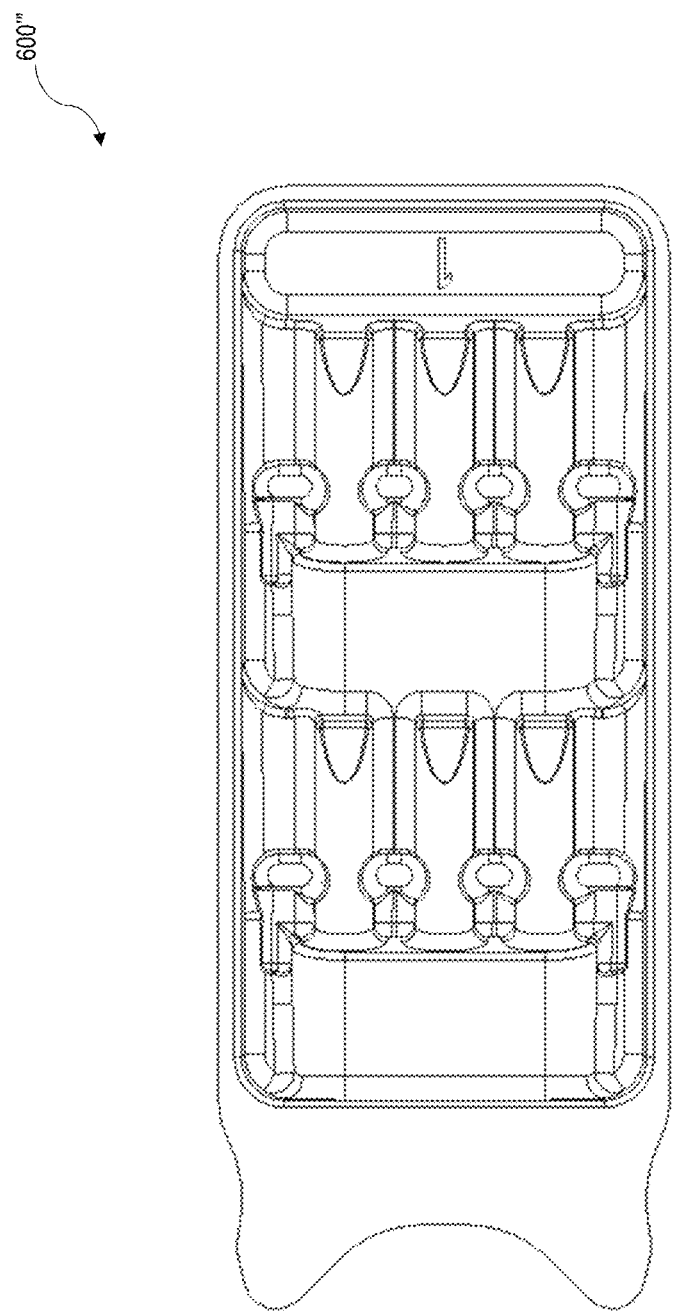
Figure 6H:
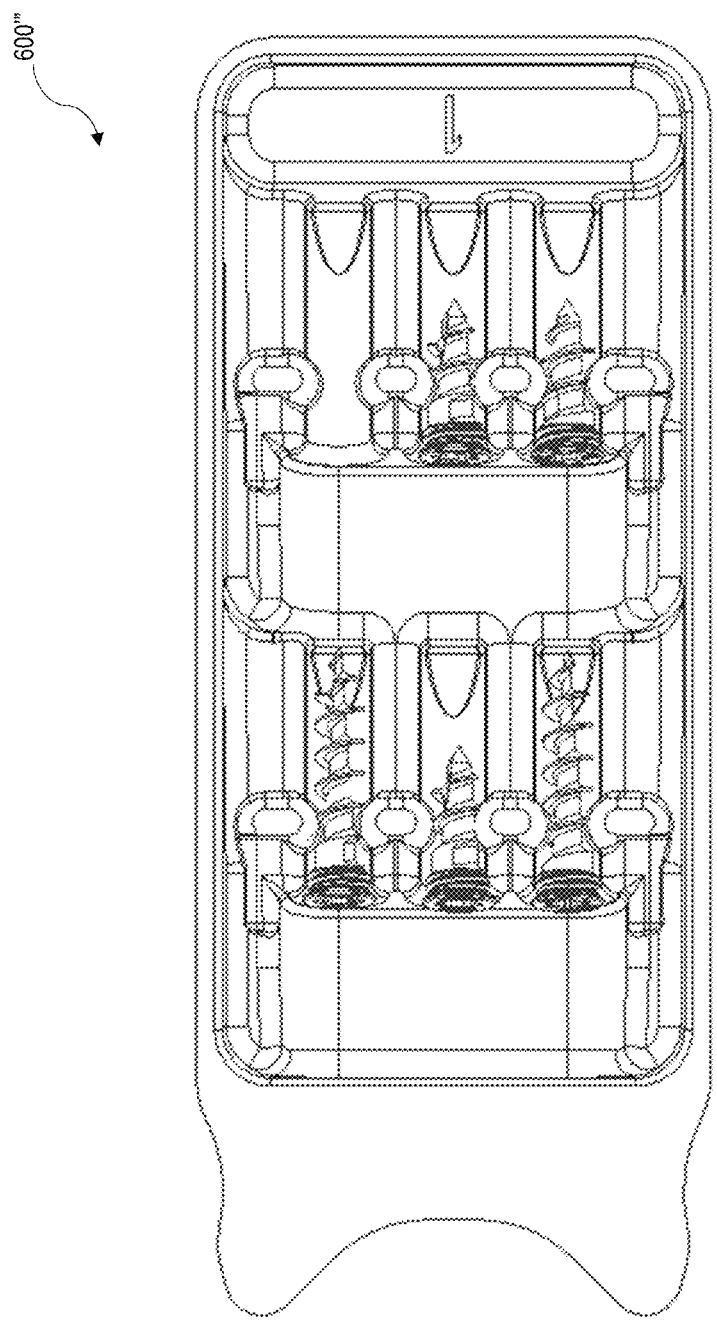
Figure 6I:
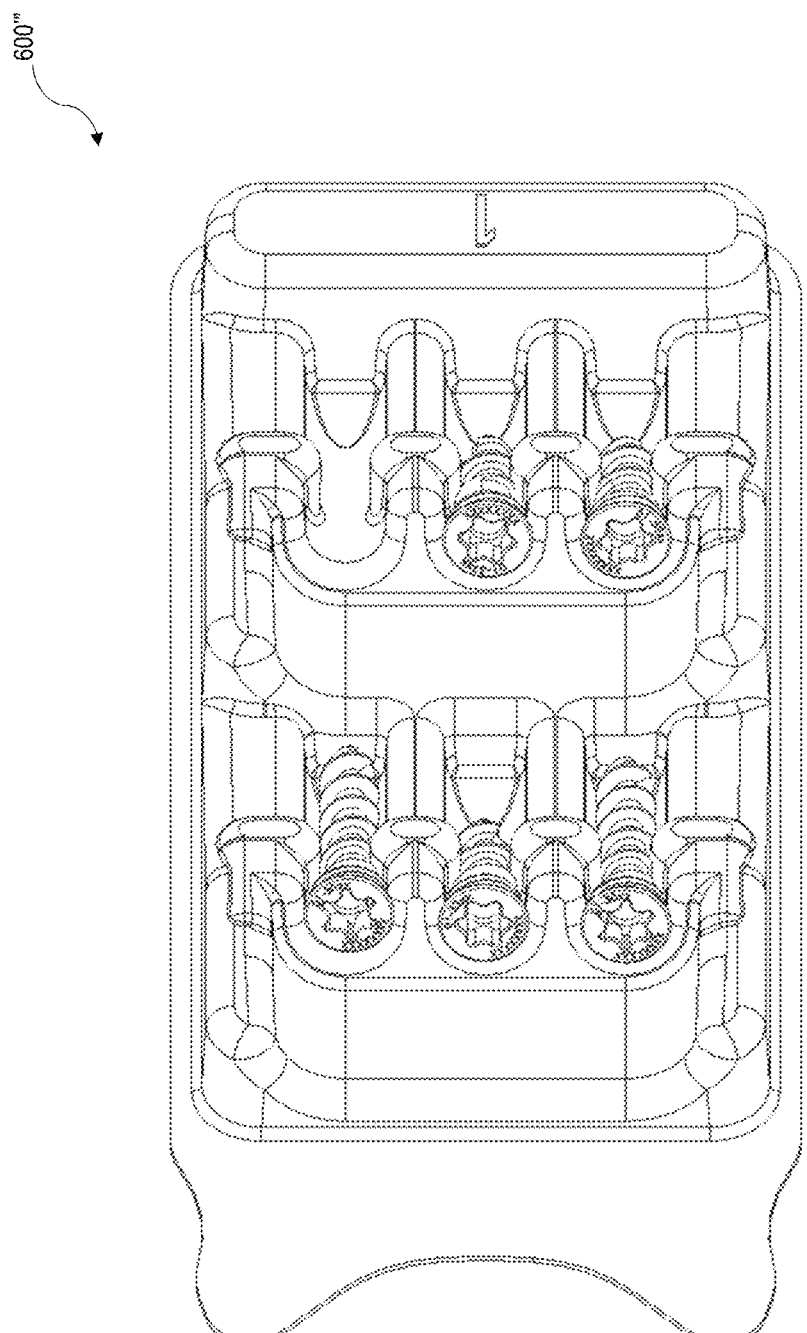

In an embodiment, the container 600' includes posts 606a, 606b (e.g. sized to frictionally engage terminal 102 of a component of the modular system 100) and/or posts 607a, 607b (e.g. sized to frictionally engage the ring connector 104 of the modular system 100). Additionally, in an embodiment, the container 600' includes posts 610, 612 to frictionally engage a component of the modular system 100 (e.g. in FIG. 6E the posts 610, 612 frictionally engage a portion of a link of the modular system 100). As shown in FIG. 6F, the container 600' can also be used to frictionally engage a plate of the modular system 100 (e.g. posts 606 frictionally engage a terminal 102 opening in the plate and/or posts 607 frictionally engage a ring connector 104 of the plate).

In an embodiment, the container 600" excludes posts but is configured and sized to frictionally engage one or more fasteners (e.g. fasteners 117, 119) of the modular system 100.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value. While example ranges are given, unless otherwise clear from the context, any contained ranges are also intended in various embodiments. Thus, a range from 0 to 10 includes the range 1 to 4 in some embodiments.

What is claimed is:

1. A modular system for assembling a structure to secure to opposite sides of a fracture in a bone of a subject, said modular system comprising at least two components selected from the group comprising:
   at least one plate with a perimeter including a plurality of openings, said perimeter defining an interior area within the plate; and
   at least one link with at least one opening along an axis of the link;
   wherein the link comprises a snap connector adjacent to the at least one opening configured to connect to a ring connector, adjacent to at least one opening of the at least one plate;
   wherein the plate comprises the ring connector adjacent to the at least one opening, said ring connector configured to removably attach to the snap connector of the at least one link prior to connecting the at least one link to the at least one plate.

2. The modular system as recited in claim 1, wherein the modular system includes at least one of:
   at least two plates and at least one link; and
   at least one plate and at least two links.

3. The modular system as recited in claim 1, wherein the structure comprises the at least one plate and a plurality of links including at least one terminal link and at least one bridging link.

4. The modular system as recited in claim 1, wherein the plate comprises the ring connector adjacent a first opening of the plurality of openings and the terminal adjacent a second opening of the plurality of openings.

5. The modular system as recited in claim 1, wherein the fracture in the bone is one of:
   a fracture in a sternum and the subject is human;
   a fracture in one of a hand and a foot and the subject is human; and
   a fracture in a skull and the subject is human.

6. The modular system as recited in claim 1, wherein the perimeter is a rectangular perimeter with the ring connector adjacent the at least one first opening at one or more corners of the rectangular perimeter;
   and wherein the plate further includes a plurality of joints to connect opposite sides of the rectangular perimeter and wherein each joint has a cross-sectional area that is less than or equal to a maximum threshold cross-sectional area capable of being cut with standard plate cutters.

7. The modular system as recited in claim 6, wherein the plate further includes the terminal adjacent at least one second opening, wherein the terminal is internally threaded to receive an externally threaded fastener to be secured in the bone and wherein the at least one second opening is positioned along a side of the rectangular perimeter between the one or more corners.

8. The modular system as recited in claim 6, wherein the modular system comprises:
   a first plate with a first rectangular perimeter defined by a first length and a first width; and
   a second plate with a second rectangular perimeter defined by a second length and a second width;
   wherein the first length is greater than the second length and the plurality of openings in the first plate is greater than the plurality of openings in the second plate.

9. The modular system as recited in claim 8,
   wherein the first width is about equal to the second width; and
   wherein the first and second width is in a range from about 10 mm to about 16 mm and wherein the first length and the second length are in a range from about 15 mm to about 75 mm.

10. The modular system as recited in claim 1,
    wherein the snap connector comprises an inner diameter that defines an internal threaded hole to receive an external threaded fastener and an outer diameter including a tapered portion and a plurality of tabs that are configured to be inwardly deflected;
    wherein the ring connector comprises a tapered portion and a chamfer;
    wherein upon engagement of the snap connector with the ring connector the tabs are configured to deflect inward and around the tapered portion of the ring connector and the tapered portion of the outer diameter of the snap connector is configured to rotatably engage the tapered portion of the ring connector;
    and wherein upon engagement of the snap connector with the ring connector the tabs are spaced apart from the chamfer by a recess and wherein the snap connector and ring connector are rotatably fixed upon the external threaded fastener being secured through the internal threaded bore and into the bone.

11. The modular system as recited in claim 1, wherein the at least one link comprises at least one of:
    a first link comprising a single opening with the snap connector adjacent the single opening and no ring connector;
    a second link comprising a pair of openings with the snap connector adjacent one of the openings and a terminal adjacent the other of the openings;
    a third link comprising a pair of openings with the snap connector adjacent one of the openings and the ring connector adjacent the other of the openings;
    a fourth link comprising a pair of openings with the ring connector adjacent both of the pair of openings; and
    a fifth link comprising a pair of openings with the snap connector adjacent both of the pair of openings.

12. The modular system as recited in claim 11, wherein the at least one link comprises the first link, the second link, the third link, the fourth link and the fifth link.

13. The modular system as recited in claim 11, wherein the at least one link further comprises:
    a sixth link comprising a plurality of openings with the snap connector adjacent one of the openings and a terminal adjacent multiple openings of the plurality of openings;
    a seventh link comprising a triangular arrangement of openings with the snap connector adjacent at least one of the openings;
    an eighth link comprising a plurality of openings with the snap connector adjacent one of the openings at a first end of the eighth link, the ring connector adjacent another of the openings at a second end of the eighth link opposite to the first end and a terminal adjacent multiple openings between the first end and the second end;
a ninth link comprising a plurality of openings with the ring connector adjacent one of the openings at a first end of the ninth link, the ring connector adjacent another of the openings at a second end of the ninth link opposite to the first end and a terminal adjacent multiple openings between the first end and the second end; and
a tenth link comprising a plurality of openings with the ring connector adjacent one of the openings at a first end of the tenth link, the ring connector adjacent another of the openings at a second end of the tenth link opposite to the first end and a plurality of terminals and a ring connector adjacent multiple openings between the first end and the second end.

14. The modular system as recited in claim 1, wherein the at least one plate comprises one or more of:
a first plate with a first rectangular perimeter and an intermediate joint that connects opposite sides of the first rectangular perimeter, wherein the ring connector is adjacent an opening at each corner of the first rectangular perimeter and the terminal is adjacent openings on opposite sides of the intermediate joint;
a second plate with a second rectangular perimeter and an intermediate joint that connects opposite sides of the second rectangular perimeter, wherein the ring connector and the terminal are adjacent openings at each corner of the second rectangular perimeter and wherein a pair of terminals are adjacent a pair of openings on one side of the intermediate joint and a pair of ring connectors are adjacent a pair of openings on another side of the intermediate joint;
a third plate with a third rectangular perimeter comprising the ring connector and the terminal adjacent openings at each corner of the third rectangular perimeter and excluding an intermediate joint;
a fourth plate with a fourth rectangular perimeter comprising the ring connector adjacent an opening at each corner of the fourth rectangular perimeter and excluding an intermediate joint;
a fifth plate with a fifth rectangular perimeter comprising the terminal adjacent each opening of the plurality of openings and excludes the ring connector.

15. The modular system as recited in claim 14, wherein the at least one plate comprises the first plate, the second plate, the third plate, the fourth plate and the fifth plate.

16. The modular system as recited in claim 1,
wherein the modular system includes a first link that includes at least one first opening with the ring connector configured to removably receive the snap connector adjacent at least one second opening of a second link so that the second link is rotatably received within the first opening; wherein the ring connector is at one or both ends of the first link; and
wherein the first link includes a first plurality of openings and the second link includes a second plurality of openings that is less than the first plurality of openings.

17. The modular system as recited in claim 1,
wherein the link includes a plurality of openings that form a triangle along a pair of linear axes that intersect at the ring connector;
wherein the link includes a plurality of openings and wherein a groove is provided between adjacent openings of the plurality of openings, wherein a depth of the groove is based on at least one of a thickness of a band or wire configured to be wrapped around the fracture in the bone and positioned in the groove and a threshold thickness sufficient to bend the link to accommodate surface anatomy of a patient;
and wherein a height of the plate and the link is less than a threshold height, wherein the threshold height is based on a distance between the bone and an inner surface of skin of the subject.

18. A method for assembling a structure to secure to opposite sides of a fracture in a bone of a subject, said method comprising:
a. determining at least one characteristic of the bone;
b. assembling a structure using the modular system of claim 1 based on the at least one characteristic of the bone;
c. aligning the assembled structure with the fracture in the bone;
d. adjusting the structure using the modular system based on the at least one characteristic of the bone and the aligning step, if the assembled structure is not aligned with the fracture; and
e. securing the assembled structure to opposite sides of the fracture in the bone if the assembled structure is aligned with the fracture.

19. The method as recited in claim 18 wherein:
step a. comprises determining at least one of a dimension of the bone and an osteoporotic quality of the bone;
wherein step a. comprises determining at least one characteristic of the bone and further determining at least one characteristic of an adjacent bone connected to the bone;
wherein the fracture in the bone is a fracture in a sternum from open heart surgery and the subject is human and wherein step a. comprises at least one of measuring a dimension of the sternum, measuring a dimension of a rib connected to the sternum, measuring an angle of the rib connected to the sternum, determining an osteoporotic quality of the sternum and determining an osteoporotic quality of the rib.

20. The method as recited in claim 19,
wherein step b comprises selecting a plate of the at least one plate of the modular system with a length based on a distance between a first location along the sternum and a second location along the sternum where the rib connects to the sternum;
wherein step b further comprises selecting a link of the at least one link of the modular system to be attached to the plate by rotatably receiving the snap connector of the link in the ring connector of the plate and wherein step b further comprises angling the link relative to the plate based on the angle of the rib relative to the sternum,
wherein the selecting the link comprises selecting a link with a length such that a snap connector or a terminal of the link extends over a portion of the rib with high osteoporotic quality,
and wherein step e comprises securing fasteners into each of the snap connectors received within each ring connector.

21. A system comprising:
a container including a tray, wherein the tray includes one or more posts within an interior of the tray; and
at least one of:
a component of the modular system of claim 1; and
a tool configured to engage the component of the modular system 1 and assemble the structure or secure the structure to the opposite sides of the fracture in a sternum bone during a cardio thoracic procedure;

wherein the posts of the tray are configured to frictionally engage the at least one of the component and the tool to secure the at least one of the component and the tool within the container.

22. A modular system for assembling a structure to secure to opposite sides of a fracture in a bone of a subject, said modular system comprising at least three components including at least three links wherein each link has at least one opening along an axis of the link and wherein each link comprises a snap or ring connector adjacent the at least one opening configured to connect to a ring or snap connector, respectively, adjacent to at least one opening of another component of the modular system, and wherein the at least three links are selected from the group comprising:

a first link comprising a single opening with the snap connector adjacent the single opening and no ring connector;

a second link comprising a pair of openings with the snap connector adjacent one of the openings and a terminal adjacent the other of the openings;

a third link comprising a pair of openings with the snap connector adjacent one of the openings and the ring connector adjacent the other of the openings;

a fourth link comprising a pair of openings with the ring connector adjacent both of the pair of openings;

a fifth link comprising a pair of openings with the snap connector adjacent both of the pair of openings;

a sixth link comprising a plurality of openings with the snap connector adjacent one of the openings and a terminal adjacent multiple openings of the plurality of openings;

a seventh link comprising a triangular arrangement of openings with the snap connector adjacent at least one of the openings;

an eighth link comprising a plurality of openings with the snap connector adjacent one of the openings at a first end of the eighth link, the ring connector adjacent another of the openings at a second end of the eighth link opposite to the first end and a terminal adjacent multiple openings between the first end and the second end;

a ninth link comprising a plurality of openings with the ring connector adjacent one of the openings at a first end of the ninth link, the ring connector adjacent another of the openings at a second end of the ninth link opposite to the first end and a terminal adjacent multiple openings between the first end and the second end; and a tenth link comprising a plurality of openings with the ring connector adjacent one of the openings at a first end of the tenth link, the ring connector adjacent another of the openings at a second end of the tenth link opposite to the first end and a plurality of terminals and a ring connector adjacent multiple openings between the first end and the second end.

* * * * *